United States Patent [19]

Biavasco et al.

[11] Patent Number: 5,705,676
[45] Date of Patent: Jan. 6, 1998

[54] CHROMOGENIC LEUCO REDOX-DYE-RELEASING COMPOUNDS FOR PHOTOTHERMOGRAPHIC ELEMENTS

[75] Inventors: Raffaella Biavasco, Savona, Italy; Lori S. Harring, Hudson, Minn.; Larry R. Krepski, White Bear Lake, Minn.; Daniel E. Mickus; Mark B. Mizen, both of St. Paul, Minn.; Sharon M. Simpson, Lake Elmo, Minn.; Cristina Soncini, Savona, Italy; Kim M. Vogel, Lake Elmo, Minn.

[73] Assignee: Minnesota Mining and Manufacturing Company, Saint Paul, Minn.

[21] Appl. No.: 558,525

[22] Filed: Nov. 16, 1995

Related U.S. Application Data

[62] Division of Ser. No. 269,400, Jun. 30, 1994, Pat. No. 5,492,804.

[51] Int. Cl.$^6$ .................. C07C 271/10; C07C 245/08; C09B 62/507
[52] U.S. Cl. .................. 560/27; 8/567; 8/573; 8/576; 8/585; 8/586; 8/602; 534/641; 534/843; 534/844; 534/847
[58] Field of Search .................. 564/39, 40, 41, 564/42; 8/585, 586, 567, 573, 576, 602; 430/224, 226; 534/641, 843, 844, 847; 560/27

[56] References Cited

U.S. PATENT DOCUMENTS

| | | |
|---|---|---|
| 1,623,499 | 4/1927 | Sheppard et al. . |
| 2,131,038 | 9/1938 | Brooker et al. . |
| 2,274,782 | 3/1942 | Gaspar . |
| 2,399,083 | 4/1946 | Waller et al. . |
| 2,410,644 | 11/1946 | Flerke et al. . |
| 2,444,605 | 7/1948 | Heimbach et al. . |
| 2,489,341 | 11/1949 | Waller et al. . |
| 2,527,583 | 10/1950 | Silberstein et al. . |
| 2,565,418 | 8/1951 | Yackel et al. . |
| 2,566,263 | 8/1951 | Trivelli et al. . |
| 2,588,765 | 3/1952 | Robijns et al. . |
| 2,597,915 | 5/1952 | Yutzy et al. . |
| 2,614,928 | 10/1952 | Yutzy et al. . |
| 2,618,556 | 11/1952 | Hewitson et al. . |
| 2,681,294 | 6/1954 | Beguin . |
| 2,694,716 | 11/1954 | Allen et al. . |
| 2,701,245 | 2/1955 | Lynn . |
| 2,728,663 | 12/1955 | Allen et al. . |
| 2,761,791 | 9/1956 | Russell . |
| 2,839,405 | 6/1958 | Jones . |
| 2,886,437 | 5/1959 | Piper . |
| 2,956,879 | 10/1960 | Van Campen . |
| 2,960,404 | 11/1960 | Milton et al. . |
| 2,992,101 | 7/1961 | Jelley et al. . |
| 3,080,254 | 3/1963 | Grant, Jr. . |
| 3,121,060 | 2/1964 | Duane . |
| 3,180,731 | 4/1965 | Roman et al. . |
| 3,206,312 | 9/1965 | Sterman et al. . |
| 3,220,839 | 11/1965 | Herz et al. . |
| 3,220,846 | 11/1965 | Tinker et al. . |
| 3,241,969 | 3/1966 | Hart et al. . |
| 3,253,921 | 5/1966 | Sawdey . |
| 3,282,699 | 11/1966 | Jones et al. . |
| 3,287,135 | 11/1966 | Anderson et al. . |
| 3,297,446 | 1/1967 | Dunn . |
| 3,297,447 | 1/1967 | McVeigh . |
| 3,330,663 | 7/1967 | Weyde et al. . |
| 3,428,451 | 2/1969 | Trevoy . |
| 3,432,300 | 3/1969 | Lestina et al. . |
| 3,457,075 | 7/1969 | Morgan et al. . |
| 3,506,444 | 4/1970 | Haist et al. . |

(List continued on next page.)

FOREIGN PATENT DOCUMENTS

| | | |
|---|---|---|
| 35262 | 9/1981 | European Pat. Off. . |
| 244 399 | 5/1990 | European Pat. Off. . |

(List continued on next page.)

OTHER PUBLICATIONS

J. Bailey et al., "The Photographic Color Development Process" in *The Chemistry of Synthetic Dyes*: K. Venkataraman, Ed.; Academic Press: New York; vol. IV, Chapter VI, 341–387 (1971).

E. Brinckman et al., "Reduction of a sensitized silver soap" in *Unconventional Imaging Processes*: Focal Press: London; pp. 74–75, 1978.

(List continued on next page.)

*Primary Examiner*—Shailendra Kumar
*Attorney, Agent, or Firm*—Walter N. Kirn; Gregory A. Evearitt

[57] ABSTRACT

A photothermographic element comprising a support bearing at least one heat-developable, photosensitive, image-forming photothermographic emulsion layer comprising:

(a) a photosensitive silver halide;
(b) a non-photosensitive, reducible source of silver;
(c) a chromogenic leuco dye reducing agent; and
(d) a binder;

wherein the chromogenic leuco dye reducing agent is a chromogenic leuco redox-dye-releasing compound of the general formula:

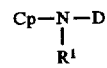

$$Cp-\underset{R^1}{N}-D$$

wherein:
(i) Cp is a coupler group;
(ii) N—D is a photographic developer group; and
(iii) $R^1$ is a —C(O)—NH—A—Dye group wherein Dye represents the chromophore of a thermally mobile dye; and A represents a single bond or a divalent linking group of the formula —X—$R^5$—L—, wherein $R^5$ is a divalent hydrocarbon chain containing up to 12 carbon atoms, L is a single bond or a divalent group that binds the chromophore of the thermally mobile dye to $R^5$, and X represents a single bond or an —$SO_2$— group.

11 Claims, No Drawings

U.S. PATENT DOCUMENTS

| | | |
|---|---|---|
| 3,531,286 | 9/1970 | Renfrew . |
| 3,573,050 | 3/1971 | Brannock et al. . |
| 3,574,627 | 4/1971 | Stern et al. . |
| 3,698,909 | 10/1972 | Lestina et al. . |
| 3,700,458 | 10/1972 | Lindholm . |
| 3,719,495 | 3/1973 | Lea . |
| 3,761,270 | 9/1973 | deMauriac et al. . |
| 3,764,337 | 10/1973 | Arai et al. . |
| 3,785,830 | 1/1974 | Sullivan et al. . |
| 3,839,049 | 10/1974 | Simons . |
| 3,847,612 | 11/1974 | Winslow . |
| 3,880,658 | 4/1975 | Lestina et al. . |
| 3,985,565 | 10/1976 | Gabrielsen et al. . |
| 4,021,240 | 5/1977 | Cerquone et al. . |
| 4,021,250 | 5/1977 | Sashihara et al. . |
| 4,022,617 | 5/1977 | McGuckin . |
| 4,042,394 | 8/1977 | Smith, Jr. et al. . |
| 4,055,428 | 10/1977 | Koyama et al. . |
| 4,060,420 | 11/1977 | Merkel et al. . |
| 4,076,539 | 2/1978 | Ikenoue et al. . |
| 4,088,496 | 5/1978 | Merkel . |
| 4,123,274 | 10/1978 | Knight et al. . |
| 4,123,282 | 10/1978 | Winslow . |
| 4,187,108 | 2/1980 | Willis . |
| 4,220,709 | 9/1980 | deMauriac . |
| 4,260,677 | 4/1981 | Winslow et al. . |
| 4,336,322 | 6/1982 | Fujita et al. . |
| 4,368,247 | 1/1983 | Fletcher, Jr. et al. . |
| 4,374,921 | 2/1983 | Frenchik . |
| 4,426,441 | 1/1984 | Adin et al. . |
| 4,455,363 | 6/1984 | Naito et al. . |
| 4,460,681 | 7/1984 | Frenchik . |
| 4,463,079 | 7/1984 | Naito et al. . |
| 4,469,773 | 9/1984 | Adin et al. . |
| 4,473,631 | 9/1984 | Hirai et al. . |
| 4,474,857 | 10/1984 | Vaughn, Jr. . |
| 4,474,867 | 10/1984 | Naito et al. . |
| 4,499,180 | 2/1985 | Hirai et al. . |
| 4,511,650 | 4/1985 | Hirai et al. . |
| 4,563,415 | 1/1986 | Brown et al. . |
| 4,594,307 | 6/1986 | Ishida . |
| 4,619,892 | 10/1986 | Simpson et al. . |
| 4,622,395 | 11/1986 | Bellus et al. . |
| 4,656,124 | 4/1987 | Komamura . |
| 4,670,374 | 6/1987 | Bellus et al. . |
| 4,708,928 | 11/1987 | Geisler . |
| 4,710,570 | 12/1987 | Thien . |
| 4,731,321 | 3/1988 | Sato et al. . |
| 4,761,361 | 8/1988 | Ozaki et al. . |
| 4,775,613 | 10/1988 | Hirai et al. . |
| 4,782,010 | 11/1988 | Mader et al. . |
| 4,883,747 | 11/1989 | Grieve et al. . |
| 4,889,932 | 12/1989 | Miller . |
| 4,923,792 | 5/1990 | Grieve et al. . |
| 4,981,775 | 1/1991 | Swain et al. . |
| 5,023,229 | 6/1991 | Evans et al. . |
| 5,064,742 | 11/1991 | Hono et al. . |
| 5,262,272 | 11/1993 | Eian et al. . |
| 5,266,452 | 11/1993 | Kitchin et al. . |
| 5,330,864 | 6/1994 | Biavasco et al. . |
| 5,432,041 | 7/1995 | Biavasco et al. ........... 430/203 |
| 5,446,010 | 8/1995 | Toyofuku et al. ........... 503/208 |
| 5,447,819 | 9/1995 | Mooberry et al. ........... 430/226 |
| 5,449,657 | 9/1995 | Takahashi . |

FOREIGN PATENT DOCUMENTS

| | | |
|---|---|---|
| 49-13224 | 2/1974 | Japan . |
| 50-17216 | 6/1975 | Japan . |
| 50-32928 | 10/1975 | Japan . |
| 51-42529 | 11/1976 | Japan . |
| 623448 | 5/1949 | United Kingdom . |
| 837095 | 6/1960 | United Kingdom . |
| 955061 | 4/1964 | United Kingdom . |
| 998949 | 7/1965 | United Kingdom . |
| 1326889 | 8/1973 | United Kingdom . |
| 1417586 | 10/1975 | United Kingdom . |
| 2100016 | 12/1982 | United Kingdom . |
| 90/00978 | 2/1990 | WIPO . |

OTHER PUBLICATIONS

G.H. Brown et al., "Azomethine Dyes. II. Color and Constitution of Acylacetamide Azomethine Dyes", *Color and Constitution of Acylacetamide Azomethine Dyes*, 79, 2919–2927 (Jun. 5, 1957).

"Carbamoyloxy substituted couplers in a photothermographic element and process", *Research Disclosure*, No. 23419, pp.314–315, Oct. 1983.

J.W. Carpenter et al., "Photothermographic silver halide systems", *Research Disclosure*, No. 17029, pp. 9–15, Jun. 1978.

D.R. Cassady et al., "Sulfonylureas and Related Compounds", *J. Org. Chem.*, 23, 923–926 (Jun. 1958).

L.J. Fleckenstein, "Color Forming Agents" in *The Theory of the Photographic Process*; T.H. James et al. (Eds.); Macmillan Publishing Co. Inc.: New York, NY; Fourth Edition, 353–354 (1977).

J.M. Harbison et al., "Chemical Sensitization and Environmental Effect", in *The Theory of the Photographic Process*; T.H. James et al. (Eds.); Macmillian Publishing Co., Inc.: New York, NY; Fourth Edition, Chapter 5, 149–169 (1977).

J.P. Kitchin et al., "Hydazine–Promoted Infectious Development of Silver Halide—An Improved Process", *J. Imag. Tech.*, 15, 282–284 (Dec. 1989).

D.H. Klosterboer, "Thermally Processed Silver Systems" in *Imaging Processes and Materials*, Neblettes Eighth Edition; J. Sturge et al. (Eds.); Van Nostrand Reinhold: New York; Chapter 9, 279–291 (1989).

P.W. Lauf, "Photothermographic Silver Halide Systems", *Research Disclosure*, No. 29963, pp. 208–214, Mar. 1989.

"Methine and Polymethine Colouring Matters" in *The Colour Index*: The Society of Dyes and Colourists: Yorkshire, England; 4, 4437 (1971).

"Photothermographic silver halide material and process", *Research Disclosure*, No. 22812, pp. 155–156, Apr. 1983.

D.J. Savage, "Synthesis and Polymerization of Dimethylaminophenyl Isocyanates" *Polymer Letters*, 12, 529–533 (1974).

G.L. Stahl et al., "General Procedure for the Synthesis of Mono–N–acylated 1,6–Diaminohexanes", *J. Org. Chem.* 43, 2285–2286 (1978).

H. Ulrich et al., *Agnew. Chem. Int. Ed.*, 5, 704–712 (1966).

CHROMOGENIC LEUCO REDOX-DYE-RELEASING COMPOUNDS FOR PHOTOTHERMOGRAPHIC ELEMENTS

This is a division of application Ser. No. 08/269,400, filed Jun. 30, 1994, now U.S. Pat. No. 5,492,804.

BACKGROUND OF THE INVENTION

1. Field of the Invention

This invention relates to photothermographic materials that form color images upon light exposure and heat development. More specifically, this invention relates to chromogenic leuco redox-dye-releasing ("RDR") compounds that are suitable for use in photothermographic imaging systems.

2. Background Art

Silver halide-containing, photothermographic imaging materials (i.e., heat-developable photographic elements) processed with heat, and without liquid development, have been known in the art for many years. These materials, also known as "dry silver" compositions or emulsions, generally comprise a support having coated thereon: (a) a photosensitive material that generates elemental silver when irradiated; (b) a non-photosensitive, reducible silver source; (c) a reducing agent for the non-photosensitive, reducible silver source; and (d) a binder. The photosensitive material is generally photographic silver halide that must be in catalytic proximity to the non-photosensitive, reducible silver source. Catalytic proximity requires an intimate physical association of these two materials so that when silver specks or nuclei are generated by irradiation or light exposure of the photographic silver halide, those nuclei are able to catalyze the reduction of the reducible silver source. It has long been understood that elemental silver ($Ag°$) is a catalyst for the reduction of silver ions, and that the photosensitive silver halide can be placed into catalytic proximity with the non-photosensitive, reducible silver source in a number of different fashions. For example, catalytic proximity can be accomplished by partial metathesis of the reducible silver source with a halogen-containing source (see, for example, U.S. Pat. No. 3,457,075); by coprecipitation of silver halide and the reducible silver source material (see, for example, U.S. Pat. No. 3,839,049); and other methods that intimately associate the photosensitive photographic silver halide and the non-photosensitive, reducible silver source.

The non-photosensitive, reducible silver source is a material that contains silver ions. Typically, the preferred non-photosensitive reducible silver source is a silver salt of a long chain aliphatic carboxylic acid having from 10 to 30 carbon atoms. The silver salt of behenic acid or fixtures of acids of similar molecular weight are generally used. Salts of other organic acids or other organic materials, such as silver imidazolates, have been proposed. U.S. Pat. No. 4,260,677 discloses the use of complexes of inorganic or organic silver salts as non-photosensitive, reducible silver sources.

In both photographic and photothermographic emulsions, exposure of the photographic silver halide to light produces small clusters of silver atoms ($Ag°$). The imagewise distribution of these clusters is known in the art as a latent image. This latent image is generally not visible by ordinary means. Thus, the photosensitive emulsion must be further processed in order to produce a visible image. The visible image is produced by the reduction of silver ions, which are in catalytic proximity to silver halide grains bearing the clusters of silver atoms, i.e., the latent image. This produces a black and white image.

As the visible image is produced entirely by elemental silver ($Ag°$), one cannot readily decrease the amount of silver in the emulsion without reducing the maximum image density. However, reduction of the amount of silver is often desirable in order to reduce the cost of raw materials used in the emulsion. One method of increasing the maximum image density in photographic and photothermographic emulsions without increasing the amount of silver in the emulsion layer is by incorporating dye-forming materials in the emulsion.

A number of methods have been proposed for obtaining color images with dry silver systems. Such methods include, for example, incorporating dye-forming coupler materials into the dry silver systems. For example, known color-forming dry silver systems include: a combination of silver benzotriazole, a magenta, yellow, or cyan dye-forming coupler, an aminophenol developing agent, a base release agent such as guanidinium trichloroacetate, and silver bromide in poly(vinyl butyral); and a combination of silver bromoiodide, sulfonamidophenol reducing agent, silver behenate, poly(vinyl butyral), an amine such as n-octadecylamine, and 2-equivalent or 4-equivalent yellow, magenta or cyan dye-forming couplers.

U.S. Pat. No. 4,021,240 discloses the use of sulfonamidophenol reducing agents and four equivalent photographic color couplers in photothermographic emulsions to produce dye images. U.S. Pat. No. 3,531,286 discloses the use of photographic phenolic or active methylene color couplers in photothermographic emulsions containing p-phenylenediamine developing agents to produce dye images. U.S. Pat. No. 4,463,079 discloses the use of sulfonamidophenol and sulfonamidonaphthol redox-dye-releasing compounds which release a diffusible dye on heat development. U.S. Pat. No. 4,474,867 discloses the use of dye-releasing couplers which, in combination with a reducing agent, release a diffusible dye on heat development. U.S. Pat. No. 4,981,775 discloses the use of redox-dye-releasing compounds, e.g., oxazines, thiazines, and azines, that release a diffusible dye on heat development.

Color images can also be formed by incorporation of leuco dyes into the emulsion. A leuco dye is the reduced form of a color-bearing dye. It is generally colorless or very lightly colored. Upon imaging, the leuco dye is oxidized, and a color-bearing dye and a reduced silver image are simultaneously formed in the exposed region. In this way, a dye-enhanced silver image can be produced. U.S. Pat. No. 4,022,617 discloses the use of leuco dyes in photothermographic emulsions. The leuco dyes are oxidized to form a color image during the heat development of the photothermographic element. Chromogenic leuco dyes having various protecting groups are described in Applicants' Assignee's copending application Ser. Nos. 07/939,093 (filed Sep. 2, 1992 now allowed) and 08/161,900 (filed Dec. 3, 1993).

Multicolor photothermographic imaging elements typically comprise two or more monocolor-forming emulsion layers (often each emulsion layer comprises a set of bilayers containing the color-forming reactants) maintained distinct from each other by barrier layers. The barrier layer overlaying one photosensitive, photothermographic emulsion layer typically is insoluble in the solvent of the next photosensitive, photothermographic emulsion layer. Photothermographic elements having at least two or three distinct color-forming emulsion layers are disclosed in U.S. Pat. Nos. 4,021,240 and 4,460,681. Various methods to produce dye images and multicolor images with leuco dyes are well known in the art as represented by U.S. Pat. Nos. 4,022,617; 3,531,286; 3,180,731; 3,761,270; 4,460,681; 4,883,747; and

*Research Disclosure*, March 1989, item 29963. Various other dye-releasing systems have been disclosed in U.S. Pat. Nos. 4,060,420; 4,731,321; 4,088,469; 4,511,650; and 4,499,180.

It is an object of the present invention to provide alternative heat developable color photographic materials capable of releasing dyes to provide clear, stable color images.

SUMMARY OF THE INVENTION

The present invention provides chromogenic leuco redox-dye-releasing ("RDR") compounds, and photothermographic elements containing these RDR compounds. The photothermographic elements of the present invention include a support bearing at least one heat-developable, photosensitive, image-forming photothermographic emulsion layer comprising:

(a) a photosensitive silver halide;

(b) a non-photosensitive, reducible source of silver;

(c) a chromogenic leuco dye reducing agent; and (d) a binder.

The chromogenic leuco dye reducing agent is a chromogenic leuco redox-dye-releasing compound. The chromogenic leuco redox-dye-releasing compound has the following general formula:

$$Cp-N-D$$
$$|$$
$$R^1$$

wherein: Cp is a coupler group, preferably a photographic coupler group; N—D is a photographic developer group, preferably a color photographic developer group; and $R^1$ is a thermally mobile dye-containing blocking group, i.e., a blocking group containing the chromophore of a thermally mobile dye. The thermally mobile dye-containing blocking group $R^1$ is of the general formula —C(O)—NH—A—Dye, wherein Dye represents the chromophore of a thermally mobile dye and A represents a single bond or a divalent linking group that binds the chromophore of the thermally mobile dye to the —C(O)—NH— blocking moiety.

Preferably A represents a divalent linking group represented by the formula —X—$R^5$—L—, wherein $R^5$ is a divalent hydrocarbon group containing up to 12 carbon atoms, L is a single bond or a divalent group that binds the chromophore of the thermally mobile dye to $R^5$, and X represents a single bond or an —$SO_2$— group. Preferred chromogenic leuco redox-dye-releasing compounds include at least one ballasting group that can be either a part of the coupler group or the developer group.

As used herein, "chromophore" refers to the light-absorbing portion of a dye molecule, i.e., the portion remaining after removal of an atom or other group from a thermally mobile dye. As used herein, "redox-dye-releasing compound" refers to a compound that releases a thermally mobile dye as a result of a redox reaction.

Particularly preferred chromogenic leuco redox-dye-releasing compounds are represented by the following general formulae:

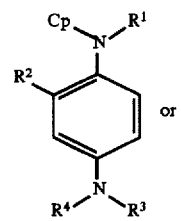

or

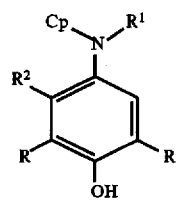

wherein: R is hydrogen or halogen (preferably Cl); $R^1$ is a —C(O)—NH—A—Dye group, wherein A represents a single bond or a divalent linking group as defined above, and Dye represents the chromophore of a thermally mobile dye; $R^2$ is a hydrogen atom, an alkoxy group (preferably containing 1–20 carbon atoms), an alkyl group (preferably containing 1–20 carbon atoms), or a ballasting group; $R^3$ and $R^4$ are each independently an aliphatic group (preferably containing 1–50 carbon atoms), an aromatic group (preferably containing 5–30 carbon atoms), a ballasting group, or a —Z—Y group, wherein Z is an alkylene group (preferably containing 1–4 carbon atoms), and Y is a cyano group, a halogen atom, an alkoxy group (preferably containing 1–20 carbon atoms), or —OH; and Cp is a coupler group (preferably a photographic coupler group). The coupler group can also include a ballasting group is so desired.

The elements of the invention are capable of producing a silver image having a negative-positive relationship to the original and a thermally mobile dye in the area corresponding to the silver image. After imagewise exposure to light, heating produces an oxidation-reduction reaction between the reducible source of silver and the dye-releasing compound, which is catalyzed by exposed, photosensitive silver halide, to form a silver image in the exposed areas. In this reaction, the redox-dye-releasing compound is oxidized, thereby cleaving the blocking group and allowing the concomitant release of a thermally mobile dye. As part of the cleavage reaction, a chromogenic dye is also formed; however, this is immobile, preferably because of the presence of a ballasting group. Accordingly, the silver image and the thermally mobile dye are present in the exposed area and a color image is obtained by transferring the thermally mobile dye to a dye-receiving layer, which may be present in the element or may be a separate dye-receiving sheet that is placed in contact with the element during heat development.

As is well understood in this technical area, a large degree of substitution is not only tolerated, but is often advisable. As a means of simplifying the discussion and recitation of certain terminology used throughout this application, the terms "group" and "moiety" are used to differentiate between chemical species that allow for substitution or which may be substituted and those which do not so allow or may not be so substituted. Thus, when the term "group" is used to describe a chemical substituent, the described chemical material includes the unsubstituted group and that group with conventional substitution. Where the term "moiety" is used to describe a chemical compound or substituent, only an unsubstituted chemical material is intended to be included. For example, the phrase "alkyl group" is intended to include not only pure open-chain and cyclic saturated hydrocarbon alkyl substituents, such as methyl, ethyl, propyl, t-butyl, cyclohexyl, adamantyl, octadecyl, and the like, but also alkyl substituents bearing further substituents known in the art, such as hydroxyl, alkoxy, vinyl, phenyl, halogen atoms (F, Cl, Br, and I), cyano, nitro, amino, carboxyl, etc. On the other hand, the phrase "alkyl moiety" is limited to the inclusion of only pure open-chain and cyclic saturated hydrocarbon alkyl substituents, such as methyl, ethyl, propyl, t-butyl, cyclohexyl, adamantyl, octadecyl, and the like.

As used herein, the term "emulsion layer" means a layer of a photothermographic element that contains a photosensitive silver salt and a non-photosensitive, reducible silver source. The term "change in color" includes an increase in optical density of at least 0.2 units between the unexposed and the exposed regions. The term "leuco dye" refers to the reduced form of a dye that is generally colorless or very lightly colored and is capable of forming a colored image upon oxidation of the leuco dye to the dye form. The term "chromogenic leuco dye" refers to a class of leuco dyes prepared by oxidative coupling of a p-phenylene-diamine compound or a p-aminophenol compound with a coupler or reductive coupling of a chromogenic dye with a blocking group. For a review of chromogenic dyes see K. Venkataraman, *The Chemistry of Synthetic Dyes*; Academic Press: New York, Vol. 4, Chapter VI.

Other aspects, advantages, and benefits of the present invention are apparent from the detailed description, the examples, and the claims.

DETAILED DESCRIPTION OF THE INVENTION

As stated above, silver halide-containing photothermographic imaging materials, i.e., "dry silver" compositions or emulsions, generally include a support having coated thereon:

(a) a photosensitive material that generates elemental silver when irradiated, e.g., a photosensitive silver halide;

(b) a non-photosensitive, reducible source of silver;

(c) a reducing agent for the non-photosensitive, reducible silver source; and (d) a binder.

Specifically, the present invention is directed to such compositions containing a chromogenic leuco redox-dye-releasing compound as the reducing agent.

The Dye-Releasing Material

The reducing agent for the reducible source of silver used in the present invention is a chromogenic leuco redox-dye-releasing compound that can be oxidized and thereby release a colored thermally mobile dye to produce a visible image. The chromogenic leuco redox-dye-releasing compounds of the present invention can be represented by the following general formula:

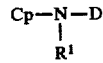

wherein $R^1$ is a thermally mobile dye-containing blocking group, "Cp" is a coupler group, preferably a photographic coupler group, and "N—D" is a photographic developer group, preferably a color photographic developer group, obtained from a developer such as a primary aromatic amine color photographic developer. Typical couplers include phenolic derivatives and materials with an active methylene group. Typical developers include p-phenylenediamine and p-aminophenol derivatives. The thermally mobile dye-containing blocking group $R^1$ is a —C(O)—NH—A—Dye group, wherein Dye is the chromophore of a thermally mobile dye and A is a single bond or a divalent linking group that binds the chromophore of the thermally mobile dye to the —C(O)—NH— blocking moiety. Preferably A is a divalent linking group of the formula —X—$R^5$—L—, wherein $R^5$ is a divalent hydrocarbon group containing up to 12 carbon atoms, L is a single bond or a divalent group that binds the chromophore of the thermally mobile dye to $R^5$, and X represents a single bond or an —SO$_2$— group.

The Cp—N—D group, i.e., chromogenic leuco portion of the redox-dye-releasing compounds of the present invention, is chosen such that it is preferably thermally immobile after release of the thermally mobile dye. Also, it is chosen such that the redox-dye-releasing compound is heat stable, substantially immobile, and does not release the thermally mobile dye upon exposure to heat only. Furthermore, it is chosen such that the redox-dye-releasing compound can be rapidly oxidized, typically upon heating to a temperature of about 80°–250° C. (176°–482° F.) for a duration of about 0.5–300 seconds in the presence of a latent image, i.e., silver atoms, and a reducible source of silver to effectively release the thermally mobile dye for image formation.

The preferred chromogenic leuco redox-dye-releasing compounds of the present invention are represented by the general Formulae I and II:

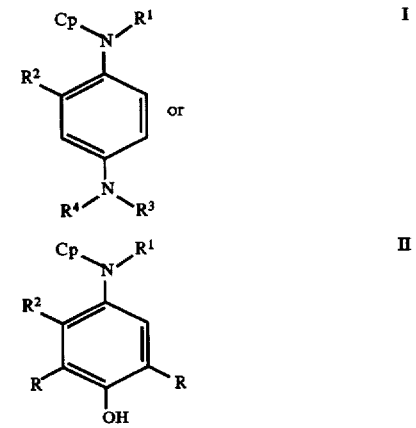

wherein:

(a) R is hydrogen or halogen (preferably Cl);

(b) $R^1$ is a —C(O)—NH—A—Dye group, wherein: Dye represents the chromophore of a thermally mobile dye; and A represents a single bond or a divalent linking group —X—$R^5$—L—, wherein $R^5$ is a divalent hydrocarbon group containing up to 12 carbon atoms, L is a single bond or a divalent group that binds the chromophore of the thermally mobile dye to $R^5$, X represents a single bond or an —SO$_2$— group;

(c) $R^2$ is a hydrogen atom, an alkoxy group (preferably containing 1–20 carbon atoms), an alkyl group (preferably containing 1–20 carbon atoms), or a ballasting group;

(d) $R^3$ and $R^4$ are each independently an aliphatic group (preferably containing 1–50 carbon atoms), an aromatic group (preferably containing 5–30 carbon atoms), a ballasting group, or a —Z—Y group, wherein Z is an alkylene group (preferably containing 1–4 carbon atoms), and Y is a cyano group, a halogen atom, an alkoxy group (preferably containing 1–20 carbon atoms), or —OH; and (e) Cp is a coupler group.

In the context of the present invention, the term "aliphatic" means a saturated or unsaturated linear, branched, or cyclic hydrocarbon group. This term is used to encompass alkyl and vinyl groups, for example. The term "alkyl" means a saturated linear, branched, or cyclic hydrocarbon group. The term "alkoxy" means an alkyl group attached to a molecule by oxygen. The terms "aromatic" or "aryl" mean a mono- or polynuclear aromatic hydrocarbon group, including alkaryl and aralkyl groups.

Chromogenic leuco redox-dye-releasing compounds of Formulae I and II can be generally prepared by selecting the appropriate coupler, developer, divalent linking group, and thermally mobile dye. The chromogenic leuco redox-dye-releasing compounds of Formula I can be prepared as described below, whereas those of Formula II can be made by analogous synthetic procedures.

In Formulae I and II, as well as all chromogenic leuco redox-dye-releasing compounds described herein, $R^1$ represents a —C(O)—NH—A—Dye group wherein A is preferably the linking group —X—$R^5$—L—. In this linking group, $R^5$ is a divalent hydrocarbon chain containing up to 12 carbon atoms. That is, it is a divalent linear, cyclic, or branched aliphatic group (preferably containing 1–12 carbon atoms), or a divalent aromatic group (preferably containing 5–12 carbon atoms). Preferably $R^5$ is an alkylene group containing 1–12 carbon atoms that can be linear, cyclic, or branched. More preferably, $R^5$ is an alkylene group containing 1–8 carbon atoms.

Examples of suitable alkylene groups include methylene, ethylene, propylene, butylene, etc. Examples of suitable arylene groups include a phenylene group, a naphthalene group, or other arylene groups of up to 12 carbon atoms. Included within the scope of the "arylene" groups, as used herein, are groups containing both aromatic and aliphatic groups in the main chain, e.g., a group such as —$CH_2$—$CH_2$—$C_6H_4$—$CH_2$—$CH_2$—. Whether aliphatic or aromatic, the $R^5$ group is allowed to have a single substituent or a plurality of substituents, which may be the same or different, that do not interfere with the release of the thermally mobile dye and migration of the thermally mobile dye to produce a visible image.

The linking group L in the thermally mobile dye-containing blocking group —C(O)—NH—X—$R^5$—L—Dye can be any group that can bond to both $R^5$ and Dye. Examples of suitable linking groups include a single bond, —$SO_2$—, —NH—, —$NHSO_2$—, —C(O)—, —C(O)—O—, —O—, —NH—C(O)—O—, —NH—C(S)—, —NH—C(O)—NH—, etc.

A thermally mobile dye is a dye that is capable of moving under the influence of heat, by diffusion through a polymeric binder and/or by sublimation across an air gap from its point of release to a receiving layer. Preferably, the dye should become mobile at a temperature of about 80°–250° C., and more preferably at a temperature of about 120°–200° C.

Suitable thermally mobile dyes for use in the compounds of the present invention, i.e., the dyes released by the chromogenic leuco redox-dye-releasing compounds of the present invention, have excellent thermal mobility in the polymeric binder and through any polymeric barrier layers, good hue, a large molar extinction coefficient, and good fastness to heat and light. Such dyes are known and disclosed, for example, in The Colour Index; The Society of Dyes and Colourites: Yorkshire, England; 1971; Vol. 4; p. 4437. Examples include azo dyes, azomethine dyes, azamethine dyes, anthraquinone dyes, naphthoquinone dyes, styryl dyes, nitro dyes, benzylidene dyes, oxazine dyes, diazine dyes, thiazine dyes, ketazine dyes, imidazole dyes, merocyanine dyes, benzodifuranone dyes, quinoline dyes, triphenylmethane dyes, as well as chromogenic dyes such as indophenol dyes and indoaniline dyes. Specific examples of useful thermally mobile dyes are the dyes listed in U.S. Pat. No. 4,336,322 (the cyan dye or dye precursor portions "COL" of compounds C-1 through C-22, the magenta dye or dye precursor portions of compounds $M_1$-1 through $M_1$-26, M-1 through M-4, $M_2$-1 through $M_2$-60, and the yellow dye or dye precursor portions of compounds Y-1 through Y-33 and 1-2); U.S. Pat. No. 4,055,428; U.S. Pat. No. 4,473,631 (the yellow and magenta dyes listed in columns 17–24); U.S. Pat. No. 4,474,857 (the yellow, magenta, and cyan dyes listed in columns 12–20); GB Patent Document No. 2,100, 016A (the yellow, magenta, and cyan dyes listed at pages 12–19); and U.S. Pat. No. 4,981,775 (the chromophores D excluding linking group A, listed in columns 4–6).

It is to be understood that either the coupler Cp or the developer group N—D can include a ballasting group. Preferably, the compounds of the present invention include at least one ballasting group. As used herein, a "ballasting group" is an organic group that reduces the thermal mobility of the chromogenic leuco redox-dye-releasing compound in the binder. The ballasting group also serves to reduce the mobility of the oxidatively formed chromogenic dye in the binder. While the size and number of carbon atoms required for the ballasting group can vary, it is preferred that the ballasting group be of a sufficient molecular weight to render the chromogenic leuco compound substantially thermally immobile at a temperature of about 80°–250° C. The molecular weight of the ballasting group must not be so high, however, that the resulting amount of the oxidized dye is insufficient to yield a dye image having a reflection optical density of at least 0.3 or a transmission optical density of at least 0.2. To meet these requirements, the ballasting group has a molecular weight of at least about 183 and no greater than about 20,000. Preferably, the ballasting group molecular weight is at least about 237 and no greater than about 15,000, more preferably at least about 337 and no greater than about 10,000, and most preferably at least about 337 and no greater than about 2,000. Representative examples of ballasting groups include long chain aliphatic groups, e.g., having at least 8 carbon atoms, aromatic rings containing a long chain aliphatic group, e.g., having at least 8 carbon atoms, preferably an aromatic ring containing a long chain alkoxy group, e.g., having at least 8 carbon atoms. Representative examples of ballasted groups that can be used in the compounds of the present invention include —O—$C_8H_{16}$, —O—$C_{12}H_{25}$, —O—$C_{18}H_{37}$, —O—$C_{22}H_{45}$, and —O—C(O)—NH—(NH—$(CH_2)_{36}$—NH—C(O)—$OCH_3$.

The ballasting group can also be incorporated within, i.e., bonded to, a polymer. Thus, either the coupler (Cp) or developer (D—N) group can be bound to a polymer. This is a particularly effective method of ballasting the redox-dye-releasing compounds of the present invention, thereby rendering the compounds substantially thermally immobile at a temperature of about 80°–250° C. and providing a high degree of differential mobility between the released thermally mobile dye, and both the remaining unreacted chromogenic leuco redox-dye-releasing compound and the remaining oxidatively formed chromogenic dye.

In Formulae I and II, $R^2$ can be a hydrogen atom, an alkoxy group, an alkyl group, or a ballasting group. Preferably $R^2$ is a hydrogen atom, an alkoxy group, or an alkyl group. More preferably, $R^2$ is a hydrogen atom, an alkoxy group containing 1–20 carbon atoms, or an alkyl group containing 1-20 carbon atoms. Most preferably, the alkyl group contains 1-4 carbon atoms. Examples of suitable alkyl and alkoxy groups include methyl, methoxy, ethyl, ethoxy, propyl, propoxy, butyl, butoxy, and the like.

In Formulae I and II, $R^3$ and $R^4$ can be an aliphatic group, an aromatic group, a ballasting group as defined above, or a —Z—Y group as defined above. Preferably, the aliphatic group contains 1-50 carbon atoms, more preferably 1-20 carbon atoms, and most preferably 1-4 carbon atoms. Of the aliphatic groups, the alkyl groups are preferred. Preferably, the aromatic group contains 5-30 carbon atoms. More preferably, the aromatic group contains 5-14 carbon atoms, and most preferably 5-10 carbon atoms. Whether aliphatic or aromatic, the $R^3$ and $R^4$ groups can have one or more substituents, which may be the same or different, that do not interfere with the release of the thermally mobile dye and resultant formation of a visible image. Examples include halogen atoms, alkoxy groups, hydroxyl, and cyano groups.

Of the dye-releasing compounds of Formulae I and II, the more preferred compounds of the present invention are the compounds of Formula I. The most preferred chromogenic leuco redox-dye-releasing compounds are compounds having Formula I wherein $R^5$ is an alkylene group containing 1-8 carbon atoms.

As noted above, Cp is a coupler group. Couplers are materials that when reacted with an oxidized photographic developer (e.g., a p-phenylenediamine, a p-aminophenol or their derivatives) couple with the oxidized developer and form dyes. The "coupler group" is that portion of the coupler remaining after reaction with the oxidized developer. The coupler group, as compared to the coupler, will have the developer residue bonded to the coupler at a position on the coupler previously occupied by a hydrogen atom or other splitting-off group at the coupling position of the coupler.

Preferably, Cp is a photographic coupler group. The term photographic coupler group has an accepted meaning within the photographic art. Examples of photographic couplers useful in the present invention are described in T. H. James, *The Theory of the Photographic Process*, Fourth Edition, 1977, Macmillan, New York. Further examples of couplers useful in the present invention are disclosed in U.S. Pat. Nos. 4,426,441 and 4,469,773, incorporated herein by reference. Representative couplers are shown in Table I:

TABLE I

Representative Couplers

Magenta Couplers

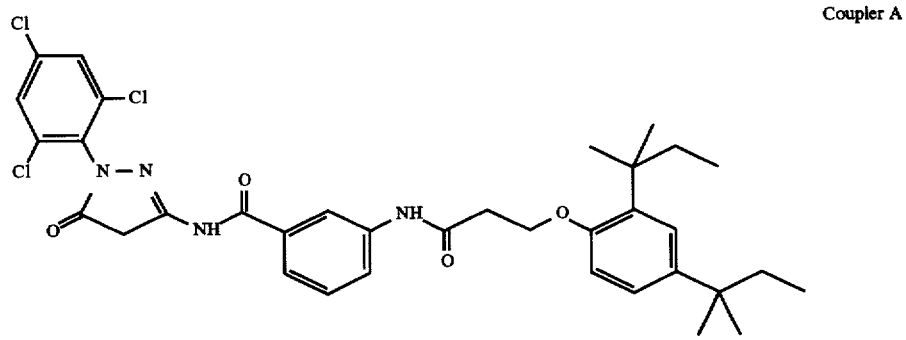

Coupler A

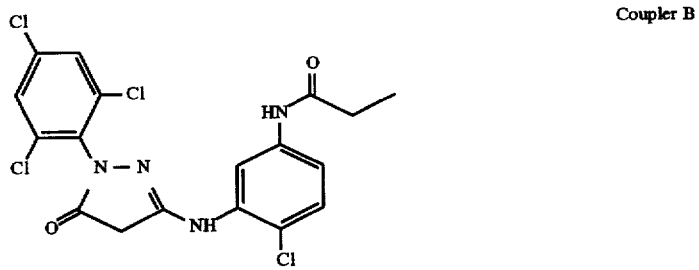

Coupler B

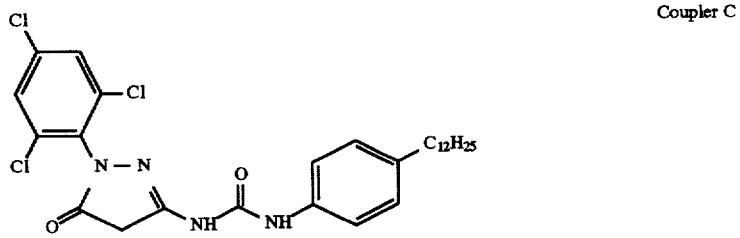

Coupler C

TABLE I-continued

Representative Couplers

Coupler D, Coupler E

Yellow Couplers

Coupler F, Coupler G, Coupler H, Coupler J

Cyan Couplers

Coupler K

TABLE I-continued

Representative Couplers

Coupler L

Coupler M

Coupler N

Examples of developers useful in the present invention are described in T. H. James, *The Theory of the Photographic Process*, Fourth Edition, 1977, Macmillan, New York; Chapter 12, pages 353 to 354. Preferred developers are those derived from p-phenylenediamines and p-aminophenols. Representative developers are shown in Table II.

TABLE II

Representative Developers

Developer A   Developer B

Developer C   Developer D

The chromogenic leuco redox-dye-releasing compounds of the present invention can be prepared either by "oxidative-coupling" or "reductive-trapping." In the oxidative-coupling method, the amine portion of a developer is blocked with a compound to form a blocked developer having the structure D—NH—C(O)—NH—A. Reaction of the blocked developer with a coupler under oxidative conditions forms a blocked chromogenic leuco dye. Further reaction of this blocked chromogenic leuco dye with a thermally mobile dye capable of reacting with the A group forms the chromogenic leuco redox-dye-releasing compound. Scheme 1 in Example 1 exemplifies this route to form chromogenic redox-dye-releasing Compound III, using Coupler K as the coupler, N,N-diethyl-p-phenylenediamine (Developer C) as the developer, and an azobenzene dye. A variation of this method involves blocking the developer with a blocking group already containing the chromophore of the thermally mobile dye to form a blocked developer having the structure D—NH—C(O)—NH—A—Dye. Reaction of the blocked developer with a coupler under oxidative conditions forms the blocked chromogenic leuco redox-dye-releasing compound. Scheme 2 in Example 2 exemplifies this route using Coupler L as the coupler and Developer B blocked with a blocking group containing the chromophore of a thermally mobile azo dye.

In the "reductive-trapping" method a coupler and a developer are reacted to form a chromogenic dye. Reduction of this dye, as for example, using hydrogen and a palladium on carbon catalyst, forms the "chromogenic leuco dye," also often referred to as the "hydrogen leuco dye." Reaction of this chromogenic leuco dye with a blocking group forms a blocked chromogenic leuco dye of structure D—N(Cp)—C(O)—NH—A. Further reaction of this blocked chromogenic leuco dye with a thermally mobile dye capable of reacting with the A group forms the chromogenic leuco redox-dye-releasing compound. As above, a variation of this method involves reaction of the hydrogen leuco dye with a blocking group already containing the chromophore of the thermally mobile dye to form the blocked chromogenic leuco redox-dye-releasing compound directly.

The chromophore of the thermally mobile dye can be added to the blocking group using a dye with a reactive functional group such as $-SO_2Cl$, $-C(O)Cl$, $-N=C=O$, $-N=C=S$, $-SO_2-N=C=O$, and the like, which is capable of reacting with a functional group on the end of the blocking group. This group typically forms the linking group L.

Representative chromogenic redox-dye-releasing compounds of the present invention are shown below. These representations are exemplary and are not intended to be limiting. They can be synthesized as shown later herein.

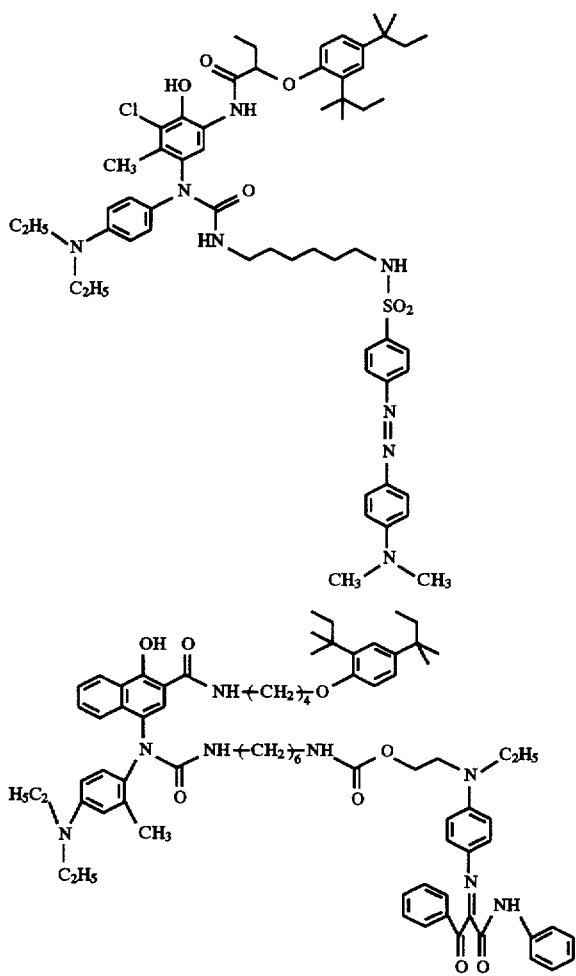

Redox-Dye-Releasing Compound IV

The dyes released from the chromogenic leuco redox-dye-releasing compounds of the present invention in the various color-forming layers should, of course, be different. A difference of at least about 60 nm in reflective maximum absorbance is preferred. More preferably, the absorbance maximum of dyes released will differ by at least about 80–100 nm. When three dyes are to be released, two should preferably differ by at least these minimums, and the third should preferably differ from at least one of the other dyes by at least about 150 nm, and more preferably, by at least about 200 nm. As previously noted, any chromogenic leuco dye that can be blocked by the thermally mobile dye-containing blocking groups of the present invention and that is capable of being oxidized by silver ion to release a dye is useful in the present invention.

The total amount of chromogenic leuco redox-dye-releasing compound used as a reducing agent utilized in the present invention should preferably be about 0.5–50 weight percent, and more preferably, about 1–25 weight percent, based upon the total weight of each individual layer in which the reducing agent is employed.

Base

In this invention, various bases or base precursors may be incorporated in the layers of light-sensitive materials or in the layers of dye-fixing materials by any desired method. For obtaining a desired dye image it is particularly advantageous to use a base or base precursor that does not reduce the shelf life of the light-sensitive materials. Such bases are particularly advantageous for enhancing the release of the thermally mobile dye.

Examples of preferred bases are amines which include trialkylamines, hydroxylamines, aliphatic polyamines, N-alkyl-substituted aromatic amines, N-hydroxyalkyl-substituted aromatic amines and bis[p-(dialkylamino)phenyl]-methanes. Further, there are betaine tetramethylammonium iodide and diaminobutane dihydrochloride as described in U.S. Pat. No. 2,410,644, and urea and organic compounds including amino acids such as 6-aminocaproic acid as described in U.S. Pat. No. 3,506,444. The base precursor is a substance which releases a basic component by heating thereby to activate light-sensitive material. Examples of typical base precursors are described in British Patent 998,949. A preferred base precursor is a salt of a carboxylic acid and an organic base. Examples of preferred carboxylic acids include trichloroacetic acid and trifluoroacetic acid. Examples of preferred bases include guanidine, piperidine, morpholine, p-toluidine and 2-picoline, etc. Guanidine trichloroacetate as described in U.S. Pat. No. 3,220,846 is particularly preferred. Ammonium phthalamates such as 2-butyl-ammonium-N-(2-butyl)phthalamate, can also be used. Such compounds are described in U.S. Pat. No. 4,088,496. Other useful bases are described in U.S. Pat. Nos. 5,064,742; 4,656,124; 4,455,363; and 3,761,270.

These bases or base precursors can be used in an amount of a broad range. A useful range is up to 50% by weight based on the amount of a dry layer coated of the light-sensitive material. A range of 0.01% by weight to 40% by weight is more preferred.

The Photosensitive Silver Halide

As noted above, the present invention includes a photosensitive silver halide in the photothermographic construction. The photosensitive silver halide can be any photosensitive silver halide, such as silver bromide, silver iodide, silver chloride, silver bromoiodide, silver chlorobromoiodide, silver chlorobromide, etc. The photosensitive silver halide can be added to the emulsion layer in any fashion so long as it is placed in catalytic proximity to the organic silver compound which serves as a source of reducible silver.

The silver halide used in the present invention may be employed without modification. However, it can be chemically and spectrally sensitized in a manner similar to that used to sensitize conventional wet process silver halide or state-of-the-art heat-developable photographic materials. For example, it may be chemically sensitized with a chemical sensitizing agent, such as a compound containing sulfur, selenium, tellurium, etc., or a compound containing gold, platinum, palladium, ruthenium, rhodium, iridium, etc., a reducing agent such as a tin halide, etc., or a combination thereof. The details of these procedures are described in T. H. James, The Theory of the Photographic Process, Fourth Edition, Chapter 5, pages 149 to 169. Suitable chemical sensitization procedures are also described in U.S. Pat. Nos. 1,623,499; 2,399,083; 3,297,447; and 3,297,446.

The photosensitive silver halides may be spectrally sensitized with various known dyes that spectrally sensitize silver halide. Non-limiting examples of sensitizing dyes that can be employed include cyanine dyes, merocyanine dyes, complex cyanine dyes, complex merocyanine dyes, holopolar cyanine dyes, hemicyanine dyes, styryl dyes, and hemioxanol dyes. Of these dyes, cyanine dyes, merocyanine dyes, and complex merocyanine dyes are particularly useful.

The light sensitive silver halide used in the present invention can be employed in a range of about 0.005 mole to about 0.5 mole and, preferably, from about 0.01 mole to about 0.15 mole per mole of non-photosensitive reducible silver salt. An appropriate amount of sensitizing dye added is generally about $10^{-10}$ to $10^{-1}$ mole, and preferably about $10^{-8}$ to $10^{-3}$ moles per mole of silver halide.

The Non-Photosensitive Reducible Silver Source Material

The non-photosensitive reducible silver source that can be used in the present invention can be any material that contains a source of reducible silver ions. Preferably, it is a silver salt which is comparatively stable to light and forms a silver image when heated to 80° C. or higher in the presence of an exposed photocatalyst (such as silver halide) and a reducing agent. Salts of organic acids, such as the silver salt of behenic acid, or other salts of organic materials, such as silver imidazolates, have been proposed. U.S. Pat. No. 4,260,677 discloses the use of complexes of inorganic or organic silver salts as non-photosensitive, reducible silver sources. Complexes of organic or inorganic silver salts, wherein the ligand has a gross stability constant for silver ion of about 4.0–10.0, are also useful in this invention.

Silver salts of organic acids, particularly silver salts of long chain fatty carboxylic acids, are preferred. The chains typically contain 10 to 30, preferably 15 to 28, carbon atoms. Suitable organic silver salts include silver salts of organic compounds having a carboxyl group. Examples thereof include a silver salt of an aliphatic carboxylic acid and a silver salt of an aromatic carboxylic acid. Preferred examples of the silver salts of aliphatic carboxylic acids include silver behenate, silver stearate, silver oleate, silver laurate, silver caproate, silver myristate, silver palmitate, silver maleate, silver fumarate, silver tartarate, silver furoate, silver linoleate, silver butyrate, silver camphorate, and mixtures thereof, etc. Silver salts that can be substituted with a halogen atom or a hydroxyl group also can be effectively used. Preferred examples of the silver salts of aromatic carboxylic acid and other carboxyl group-containing compounds include: silver benzoate, a silver-substituted benzoate, such as silver 3,5-dihydroxybenzoate, silver o-methylbenzoate, silver m-methylbenzoate, silver p-methylbenzoate, silver 2,4-dichlorobenzoate, silver acetamidobenzoate, silver p-phenylbenzoate, etc.; silver gallate; silver tannate; silver phthalate; silver terephthalate; silver salicylate; silver phenylacetate; silver pyromellilate; a silver salt of 3-carboxymethyl-4-methyl-4-thiazoline-2-thione or the like as described in U.S. Pat. No. 3,785,830; and a silver salt of an aliphatic carboxylic acid containing a thioether group as described in U.S. Pat. No. 3,330,663.

Silver salts of compounds containing mercapto or thione groups and derivatives thereof can also be used. Preferred examples of these compounds include: a silver salt of 3-mercapto-4-phenyl-1,2,4-triazole; a silver salt of 2-mercaptobenzimidazole; a silver salt of 2-mercapto-5-aminothiadiazole; a silver salt of 2-(2-ethylglycolamido) benzothiazole; a silver salt of thioglycolic acid, such as a silver salt of a S-alkylthioglycolic acid (wherein the alkyl group has from 12 to 22 carbon atoms); a silver salt of a dithiocarboxylic acid such as a silver salt of dithioacetic acid; a silver salt of thioamide; a silver salt of 5-carboxylic-1-methyl-2-phenyl-4-thiopyridine; a silver salt of mercaptotriazine; a silver salt of 2-mercapto-benzoxazole; a silver salt as described in U.S. Pat. No. 4,123,274, for example, a silver salt of a 1,2,4-mercaptothiazole derivative, such as a silver salt of 3-amino-5-benzylthio-1,2,4-thiazole; and a silver salt of a thione compound, such as a silver salt of 3-(2-carboxyethyl)-4-methyl-4-thiazoline-2-thione. Silver salts of acetylenes can also be used. Silver acetylides are described in U.S. Pat. Nos. 4,761,361 and 4,775,613.

Furthermore, a silver salt of a compound containing an imino group can be used. Preferred examples of these compounds include: silver salts of benzotriazole and substituted derivatives thereof, for example, silver methylbenzotriazole and silver 5-chlorobenzotriazole, etc.; silver salts of 1,2,4-triazoles or 1-H-tetrazoles as described in U.S. Pat. No. 4,220,709; and silver salts of imidazoles and imidazole derivatives.

It is also convenient to use silver half soaps. A preferred example of a silver half soap is an equimolar blend of silver behenate and behenic acid, which analyzes for about 14.5% silver and which is prepared by precipitation from an aqueous solution of the sodium salt of commercial behenic acid.

Transparent sheet materials made on transparent film backing require a transparent coating. For this purpose a silver behenate full soap, containing not more than about 4 or 5 percent of free behenic acid and analyzing for about 25.2 percent silver, can be used. The method used for making silver soap dispersions is well known in the art and is disclosed in *Research Disclosure*, April 1983, item 22812; *Research Disclosure*, October 1983, item 23419; and U.S. Pat. No. 3,985,565.

The silver halide may be "pre-formed" and mixed with the organic silver salt in a binder prior to use to prepare a coating solution. The silver halide may be pre-formed by any means, e.g., in accordance with U.S. Pat. No. 3,839,049. For example, it is effective to blend the silver halide and organic silver salt using a homogenizer for a long period of time. Materials of this type are often referred to as "pre-formed emulsions." Methods of preparing these silver halide and organic silver salts and manners of blending them and methods of forming pre-formed emulsions are described in *Research Disclosure*, June, 1978, item 17029; U.S. Pat. Nos. 3,700,458 and 4,076,539; and Japanese patent application Nos. 13224/74, 17216/75, and 42529/76.

Pre-formed silver halide emulsions when used in the material of this invention can be unwashed or washed to remove soluble salts. In the latter case the soluble salts can be removed by chili-setting and leaching or the emulsion can be coagulation washed, e.g., by the procedures described in U.S. Pat. Nos. 2,618,556; 2,614,928; 2,565,418; 3,241,969; and 2,489,341. The silver halide grains may have any crystalline habit including, but not limited to, cubic, tetrahedral, orthorhombic, tabular, laminar, platelet, etc. The silver halide grains may have a uniform ratio of halide throughout; they may have a graded halide content, with a continuously varying ratio of, for example, silver bromide and silver iodide; or they may be of the core-shell-type, having a discrete core of one halide ratio, and a discrete shell of another halide ratio.

It is also effective to use an in situ process, i.e., a process in which a halogen-containing compound is added to an organic silver salt to partially convert the silver of the organic silver salt to silver halide.

The silver halide and the non-photosensitive reducible silver source material that form a starting point of development should be in catalytic proximity, i.e., reactive association. By "catalytic proximity" or "reactive association" is meant that they should be in the same layer, in adjacent layers, or in layers separated from each other by an intermediate layer having a thickness of less than 1 micrometer (1 μm). It is preferred that the silver halide and the non-photosensitive reducible silver source material be present in the same layer.

Photothermographic emulsions containing pre-formed silver halide in accordance with this invention can be sensitized with chemical sensitizers, or with spectral sensitizers as described above.

The source of reducible silver material generally constitutes about 15 to about 70 percent by weight of the emulsion layer. It is preferably present at a level of about 30 to about 55 percent by weight of the emulsion layer.

The Binder

The photosensitive silver halide, the non-photosensitive reducible source of silver, the chromogenic leuco redox-dye-releasing compound, and other addenda used in the present invention are generally added to at least one binder. The binder(s) that can be used in the present invention can be employed individually or in combination with one another. It is preferred that the binder be selected from polymeric materials, such as, for example, natural and synthetic resins that are sufficiently polar to hold the other ingredients of the emulsion in solution or suspension. The binder can be hydrophilic or hydrophobic, preferably it is hydrophobic.

A typical hydrophilic binder is a transparent or translucent hydrophilic colloid. Examples of hydrophilic binders include: a natural substance, for example, a protein such as gelatin, a gelatin derivative, a cellulose derivative, etc.; a polysaccharide such as starch, gum arabic, pullulan, dextrin, etc.; and a synthetic polymer, for example, a water-soluble polyvinyl compound such as polyvinyl alcohol, polyvinyl pyrrolidone, acrylamide polymer, etc. Another example of a hydrophilic binder is a dispersed vinyl latex compound which is used for the purpose of increasing dimensional stability of a photographic element.

Examples of typical hydrophobic binders are polyvinyl acetals, polyvinyl chloride, polyvinyl acetate, cellulose acetate, polyolefins, polyesters, polystyrene, polyacrylonitrile, polycarbonates, methacrylate copolymers, maleic anhydride ester copolymers, butadiene-styrene copolymers, and the like. Copolymers, e.g. terpolymers, are also included in the definition of polymers. The polyvinyl acetals, such as polyvinyl butyral and polyvinyl formal, and vinyl copolymers such as polyvinyl acetate and polyvinyl chloride are particularly preferred.

The binders are preferably used at a level of about 20–80 percent by weight of the emulsion layer, and more preferably at a level of about 30–55 percent by weight. Where the proportions and activities of the chromogenic leuco compounds of the present invention require a particular developing time and temperature, the binder should be able to withstand those conditions. Generally, it is preferred that the binder not decompose or lose its structural integrity at 200° F. (90° C.) for 30 seconds, and more preferred that it not decompose or lose its structural integrity at 300° F. (149° C.) for 30 seconds.

Optionally, these polymers may be used in combination of two or more thereof. Such a polymer is used in an amount sufficient to carry the components dispersed therein, that is, within the effective range of the action as the binder. The effective range can be appropriately determined by one skilled in the art.

Photothermographic Formulations

The formulation for the photothermographic emulsion layer can be prepared by dissolving and dispersing the binder, the photosensitive silver halide, the non-photosensitive reducible source of silver, the chromogenic leuco compound reducing agent for the non-photosensitive reducible silver source, and optional additives, in an inert organic solvent, such as, for example, toluene, 2-butanone, or tetrahydrofuran.

The use of "toners" or derivatives thereof which improve the image, is highly desirable, but is not essential to the element. Toners can be present in an amount of about 0.01–10 percent by weight of the emulsion layer, preferably about 0.1–10 percent by weight. Toners are well known materials in the photothermographic art, as shown in U.S. Pat. Nos. 3,080,254; 3,847,612; and 4,123,282.

Examples of toners include: phthalimide and N-hydroxyphthalimide; cyclic imides such as succinimide, pyrazoline-5-ones, quinazolinone, 1-phenylurazole, 3-phenyl-2-pyrazoline-5-one, and 2,4-thiazolidinedione; naphthalimides such as N-hydroxy-1,8-naphthalimide; cobalt complexes such as cobaltic hexamine trifluoroacetate; mercaptans such as 3-mercapto-1,2,4-triazole, 2,4-dimercaptopyrimidine, 3-mercapto-4,5-diphenyl-1,2,4-triazole and 2,5-dimercapto-1,3,4-thiadiazole; N-(aminomethyl)aryldicarboximides such as (N,N-dimethylaminomethyl)phthalimide, and N-(dimethylaminomethyl)naphthalene-2,3-dicarboximide; a combination of blocked pyrazoles, isothiuronium derivatives, and certain photobleach agents such as a combination of N,N'-hexamethylene-bis(1-carbamoyl-3,5-dimethylpyrazole), 1,8-(3,6-diaza-octane)bis(isothiuronium)trifluoroacetate, and 2-(tribromomethylsulfonyl benzothiazole); merocyanine dyes such as 3-ethyl-5-[(3-ethyl-2-benzothiazolinylidene)-1-methyl-ethylidene]-2-thio-2,4-o-azolidinedione; phthalazinone, phthalazinone derivatives, or metal salts or these derivatives, such as 4-(1-naphthyl)phthalazinone, 6-chlorophthalazinone, 5,7-dimethoxyphthalazinone, and 2,3-dihydro-1,4-phthalazinedione; a combination of phthalazine plus one or more phthalic acid derivatives such as phthalic acid, 4-methylphthalic acid, 4-nitrophthalic acid, and tetrachlorophthalic anhydride, quinazolinediones, benzoxazine or naphthoxazine derivatives; rhodium complexes functioning not only as tone modifiers but also as sources of halide ion for silver halide formation in situ, such as ammonium hexachlororhodate (III), rhodium bromide, rhodium nitrate, and potassium hexachlororhodate (III); inorganic peroxides and persulfates such as ammonium peroxydisulfate and hydrogen peroxide; benzoxazine-2,4-diones such as 1,3-benzoxazine-2,4-dione, 8-methyl-1,3-benzoxazine-2,4-dione, and 6-nitro-1,3-benzoxazine-2,4-dione; pyrimidines and asym-triazines such as 2,4-dihydroxypyrimidine, 2-hydroxy-4-aminopyrimidine, and azauracil; and tetrazapentalene derivatives such as 3,6-dimercapto-1,4-diphenyl-1H,4H-2,3a,5,6a-tetrazapentalene and 1,4-di-(o-chlorophenyl)-3,6-dimercapto-1H,4H-2,3a,5, 6a-tetrazapentalene.

The photothermographic elements used in this invention can be further protected against the additional production of fog and can be stabilized against loss of sensitivity during storage. While not necessary for the practice of the invention, it may be advantageous to add mercury (II) salts to the emulsion layer(s) as an antifoggant. Preferred mercury (II) salts for this purpose are mercuric acetate and mercuric bromide.

Other suitable antifoggants and stabilizers, which can be used alone or in combination, include the thiazolium salts described in U.S. Pat. Nos. 2,131,038 and 2,694,716; the azaindenes described in U.S. Pat. No. 2,886,437; the triazaindolizines described in U.S. Pat. No. 2,444,605; the mercury salts described in U.S. Pat. No. 2,728,663; the urazoles described in U.S. Pat. No. 3,287,135; the oximes described in British Patent No. 623,448; the polyvalent metal salts described in U.S. Pat. No. 2,839,405; the isothiourea compounds described in U.S. Pat. No. 3,220,839; and palladium, platinum and gold salts described in U.S. Pat. Nos. 2,566,263 and 2,597,915.

Photothermographic elements of the invention can contain plasticizers and lubricants such as polyalcohols and diols of the type described in U.S. Pat. No. 2,960,404; fatty acids or esters such as those described in U.S. Pat. Nos. 2,588,765 and 3,121,060; and silicone resins such as those described in British Patent No. 955,061.

The photothermographic elements of the present invention can also include image dye stabilizers. Such image dye stabilizers are illustrated by U.K. Patent No. 1,326,889; and U.S. Pat. Nos. 3,432,300; 3,574,627; 3,573,050; 3,764,337; and 4,042,394.

Photothermographic elements according to the present invention can be used in photographic elements that contain light-absorbing materials, antihalation, acutance, and filter dyes such as those described in U.S. Pat. Nos. 3,253,921; 2,274,782; 2,527,583; 2,956,879 and 5,266,452. If desired, the dyes can be mordanted, for example, as described in U.S. Pat. No. 3,282,699. They can also contain matting agents such as starch, titanium dioxide, zinc oxide, silica, and polymeric beads including beads of the type described in U.S. Pat. Nos. 2,992,101 and 2,701,245. Furthermore they can also contain antistatic or conducting layers, such as layers that comprise soluble salts, e.g., chlorides, nitrates, etc., evaporated metal layers, ionic polymers such as those described in U.S. Pat. No. 3,206,312 or insoluble inorganic salts such as those described in U.S. Pat. No. 3,428,451.

Photothermographic Constructions

The photothermographic elements of this invention can be constructed of one or more layers on a substrate. Single layer constructions should contain the silver halide, the non-photosensitive, reducible silver source material, the chromogenic leuco redox-dye-releasing (RDR) compound, and binder as well as optional materials such as toners, coating aids, and other adjuvants. Two-layer constructions should contain silver halide and non-photosensitive, reducible silver source in one emulsion layer (usually the layer adjacent to the substrate) and some of the other ingredients in the second layer or both layers, although two layer constructions comprising a single emulsion layer coating containing all the ingredients and a protective topcoat are envisioned. Multicolor photothermographic dry silver constructions can contain sets of these bilayers for each color or they can contain all ingredients within a single layer, as described in U.S. Pat. No. 4,708,928. In the case of multilayer, multicolor photothermographic elements, the various emulsion layers are generally maintained distinct from each other by the use of functional or non-functional barrier layers between the various photosensitive layers, as described in U.S. Pat. No. 4,460,681.

Development conditions will vary, depending on the construction used, but will typically involve heating the imagewise exposed material at a suitably elevated temperature. When used in a photothermographic element, the latent image obtained after exposure of the heat-sensitive construction can be developed by heating the material at a moderately elevated temperature of, for example, about 80°–250° C., preferably about 120°–200° C., for a sufficient period of time, generally about 1 second to about 2 minutes. Heating may be carried out by the typical heating means such as a hot plate, an iron, a hot roller, a heat generator using carbon or titanium white, or the like.

In some methods, the development is carried out in two steps. Thermal development takes place at a higher temperature, e.g., about 150° C. for about 10 seconds, followed by thermal diffusion at a lower temperature, e.g., about 80° C., in the presence of a transfer solvent. The second heating step at the lower temperature prevents further development and allows the dyes that are already released to diffuse out of the emulsion layer to the receptor layer.

Photothermographic emulsions used in this invention can be coated by various coating procedures including wire wound rod coating, dip coating, air knife coating, curtain coating, or extrusion coating using hoppers of the type described in U.S. Pat. No. 2,681,294. If desired, two or more layers can be coated simultaneously by the procedures described in U.S. Pat. No. 2,761,791 and British Patent. No. 837,095. Typical wet thickness of the emulsion layer can be about 10–100 micrometers (μm), and the layer can be dried in forced air at a temperature of about 20°–100° C. It is preferred that the thickness of the layer be selected to provide maximum image densities greater than about 0.2, and, more preferably, in the range of about 0.5 to 2.5, as measured by a MacBeth Color Densitometer Model TD 504 using the color filter complementary to the dye color.

Additionally, it may be desirable in some instances to coat different emulsion layers on both sides of a transparent substrate, especially when it is desirable to isolate the imaging chemistries of the different emulsion layers.

Barrier layers, preferably comprising a polymeric material, can also be present in the photothermographic element of the present invention. Polymers for the material of the barrier layer can be selected from natural and synthetic polymers such as gelatin, polyvinyl alcohols, polyacrylic acids, sulfonated polystyrene, and the like. The polymers can optionally be blended with barrier aids such as silica. Alternatively, the formulation can be spray-dried or encapsulated to produce solid particles, which can then be redispersed in a second, possibly different, binder and then coated onto the support. The formulation for the emulsion layer can also include coating aids such as fluoroaliphatic polyesters.

Photothermographic emulsions used in the invention can be coated on a wide variety of supports. The support or substrate can be selected from a wide range of materials depending on the imaging requirement. Substrates may be transparent or opaque. Typical supports include polyester film, subbed polyester film, poly(ethylene terephthalate) film, cellulose nitrate film, cellulose ester film, polyvinyl acetal film, polycarbonate film and related or resinous materials, as well as glass, paper, metal, and the like. Typically, a flexible support is employed, especially a paper support, which can be partially acetylated or coated with baryta and/or an α-olefin polymer, particularly a polymer of an α-olefin containing 2 to 10 carbon atoms such as polyethylene, polypropylene, ethylene-butene copolymers, and the like. Preferred polymeric materials for the support include polymers having good heat stability, such as polyesters. A particularly preferred polyester is poly(ethylene terephthalate). A substrate with a backside resistive heating layer can also be used in color photothermographic imaging systems such as shown in U.S. Pat. Nos. 4,460,681 and 4,374,921.

The Dye-Receiving Layer

The photothermographic element includes a dye-receiving layer. Thermally mobile dyes derived from photothermographic elements employing chromogenic redox-dye-releasing compounds capable of being oxidized to release a thermally mobile dye typically migrate or are transferred to a dye-receiving or an image-receiving layer.

Dyes released during thermal development of light-exposed regions of the emulsion layers migrate under development conditions into an image-receiving, i.e., dye-receiving, layer wherein they are retained. The dye-receiving layer can be composed of a polymeric material having affinity for the dyes employed. Necessarily, it will vary depending on the ionic or neutral characteristics of the dyes.

The dye-receiving layer of this invention can be any flexible or rigid, transparent layer made of thermoplastic polymer. The dye-receiving layer preferably has a thickness of at least about 0.1 µm, more preferably about 1–10 µm, and a glass transition temperature ($T_g$) of about 20°–200° C. In the present invention, any thermoplastic polymer or combination of polymers can be used, provided the polymer is capable of absorbing and fixing the dye. The polymer may include dye mordants to fix the dye. Alternatively, the polymer itself may act as a dye mordant in which case no additional fixing agents are required. Thermoplastic polymers that can be used to prepare the dye-receiving layer include polyesters, such as polyethylene terephthalates; polyolefins, such as polyethylene; cellulosics, such as cellulose acetate, cellulose butyrate, and cellulose propionate; polystyrene; polyvinyl chloride; polyvinylidine chloride; polyvinyl acetate; copolymer of vinyl chloride-vinyl acetate; copolymer of vinylidene chloride-acrylonitrile; copolymer of styrene-acrylonitrile; and the like.

The dye-receiving layer can be prepared by dissolving at least one thermoplastic polymer in an organic solvent (e.g., 2-butanone, acetone, tetrahydrofuran) and applying the resulting solution to a support base or substrate by various coating methods known in the art, such as curtain coating, extrusion coating, dip coating, air-knife coating, hopper coating, and any other coating method used for coating solutions. After the solution is coated, the dye-receiving layer is dried (e.g., in an oven) to drive off the solvent. The dye-receiving layer can be a permanent part of the construction or it can be removable. When an integral part of the photothermographic element it is usually separated from the photothermographic emulsion layers by an opacifying layer. Alternatively, the dye-receiving layer can be strippably adhered to the photothermographic element and subsequently peeled from the construction. Strippable dye-receiving layers are described in U.S. Pat. No. 4,594,307.

Selection of the binder and solvent to be used in preparing the emulsion layer significantly affects the strippability of the dye-receiving layer from the photosensitive element. Preferably, the binder for the image-receiving layer is impermeable to the solvent used for coating the emulsion layer and is incompatible with the binder used for the emulsion layer. The selection of the preferred binders and solvents results in weak adhesion between the emulsion layer and the dye-receiving layer and promotes good strippability of the emulsion layer.

The photothermographic element can also include coating additives to improve the strippability of the emulsion layer. For example, fluoroaliphatic polyesters dissolved in ethyl acetate can be added in an amount of about 0.02–0.5 weight percent of the emulsion layer, preferably about 0.1–0.3 weight percent. A representative example of such a fluoroaliphatic polyester is "Fluorad™ FC 431" (a fluorinated surfactant available from Minnesota Mining and Manufacturing Company, St. Paul, Minn.). Alternatively, a coating additive can be added to the dye-receiving layer in the same weight range to enhance strippability. No solvents need to be used in the stripping process. The strippable layer preferably has a delaminating resistance of about 1–50 g/cm and a tensile strength at break greater than, preferably at least two times greater than, its delaminating resistance.

Preferably, the dye-receiving layer is adjacent to the emulsion layer in order to facilitate transfer of the dye that is released after the imagewise exposed emulsion layer is subjected to thermal development, for example, in a heated shoe-and-roller-type or heated drum-type heat processor.

Photothermographic multi-layer constructions containing blue-sensitive emulsions containing a redox-yellow-dye-releasing compound can be overcoated with green-sensitive emulsions containing a redox-magenta-dye-releasing compound. These layers can in turn be overcoated with a red-sensitive emulsion layer containing a redox-cyan-dye-releasing compound. Imaging and heating release the yellow, magenta, and cyan dyes in an imagewise fashion. Color-forming layers can be maintained distinct from each other by the use of functional or non-functional barrier layers between the various photosensitive layers as described in U.S. Pat. No. 4,460,681. False color address, such as that shown in U.S. Pat. No. 4,619,892, can also be used rather than blue-yellow, green-magenta, or red-cyan relationships between sensitivity and dye-release. False color address is particularly useful when imaging is performed using longer wavelength light sources, especially red or near infrared light sources, to enable digital address by lasers and laser diodes. The dyes so released may migrate to a dye-receiving layer.

If desired, the colored dyes released in the emulsion layer can be transferred onto a separately coated dye-receiving sheet by placing the exposed emulsion layer in intimate face-to-face contact with the dye-receiving sheet and heating the resulting composite construction. Good results can be achieved in this second embodiment when the layers are in uniform contact for a period of time of about 0.5–300 seconds at a temperature of about 80°–250° C.

In another embodiment, a multi-colored image can be prepared by superimposing in register a single dye-receiving sheet successively with two or more imagewise exposed photothermographic elements, each of which releases a dye of a different color, and heating to transfer the thus released dyes as described above. This method is particularly suitable for the production of color proofs especially when the dyes released have hues that match the internationally agreed standards for color reproduction. These are known as Standard Web Offset Press or SWOP colors. Dyes with this property are disclosed in U.S. Pat. No. 5,023,229. In this embodiment, the photothermographic elements are preferably all sensitized to the same wavelength range regardless of the color of the dye released. For example, the elements can be sensitized to ultraviolet radiation with a view toward contact exposure on conventional printing frames, or they can be sensitized to longer wavelengths, especially red or near infra-red, to enable digital address by lasers and laser diodes. As noted above, false color address is again particularly useful when imaging is performed using longer wavelength light sources, especially red or near infrared light sources, to enable digital address by lasers and laser diodes.

The complete disclosures of all patents, patent documents, and publications listed herein are incorporated by reference. Reasonable modifications and variations are possible from the foregoing disclosure without departing from either the spirit or scope of the present invention as defined by the claims. Objects and advantages of this invention will now be illustrated by the following examples, but the particular materials and amounts thereof recited in these examples, as well as other conditions and details, should not be construed to unduly limit this invention.

EXAMPLES

All materials used in the following examples were readily available from standard commercial sources, such as Aldrich Chemical Co. (Milwaukee, Wis.) unless otherwise specified. All percentages are by weight unless otherwise indicated.

Speed-1 is the log exposure (in ergs) corresponding to a density of 0.20 above Dmin.

Speed-2 is the log Exposure (in ergs) corresponding to a density of 0.60 above Dmin.

AC-1 (Average Contrast-1) is the slope of a line joining the density points at 0.3 to 0.9 above Dmin.

Dabsyl chloride is 4-(dimethylamino)azobenzene-4'-sulfonyl chloride t—BOC is tert-butoxycarbonyl (t—Bu—O—C(O)—)

Example 1

Preparation of Redox-Yellow Dye-Releasing Compound

The synthetic route to redox-dye-release compound III is shown in Scheme 1. The synthesis of 4-(diethylaminophenyl)isocyanate (2) from carbamate (1) is described in *Polymer Letters*, 12, 529 (1974). Carbamate (1) was treated with chlorotrimethylsilane and triethylamine. When the reaction was complete the mixture was filtered to remove triethylamine in toluene. Isocyanate (2) was purified by distillation and the yield was somewhat low; however, it was found that this purification step is not necessary. The synthesis of mono-protected diamine (3) is described in *Journal of Organic Chemistry*, 43, 2285 (1978). Treatment of the solution of isocyanate (2) with diamine (3) gave blocked developer (4). This is a protected form of Developer C shown above. Oxidative coupling of blocked developer (4) with Coupler K (5) using potassium ferrocyanide and potassium ferricyanide gave leuco dye intermediate (6). The t-BOC protecting group of leuco dye intermediate (6) was removed with trifluoroacetic acid to give leuco dye intermediate (7). Leuco dye intermediate (7) was converted to redox-dye-releasing compound III upon treatment with dabsyl chloride (8).

Scheme I - Preparation of Compound III

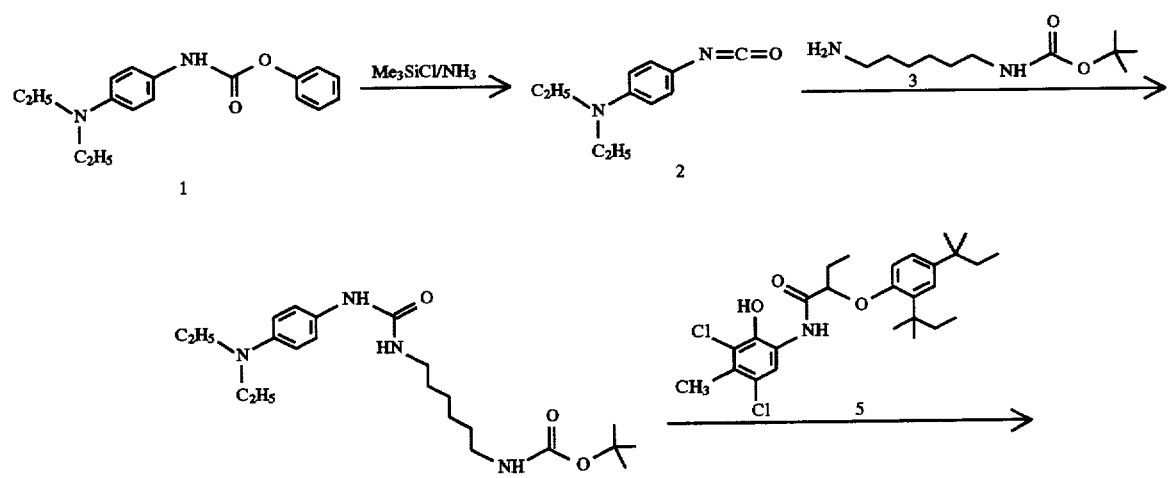

-continued
Scheme I - Preparation of Compound III

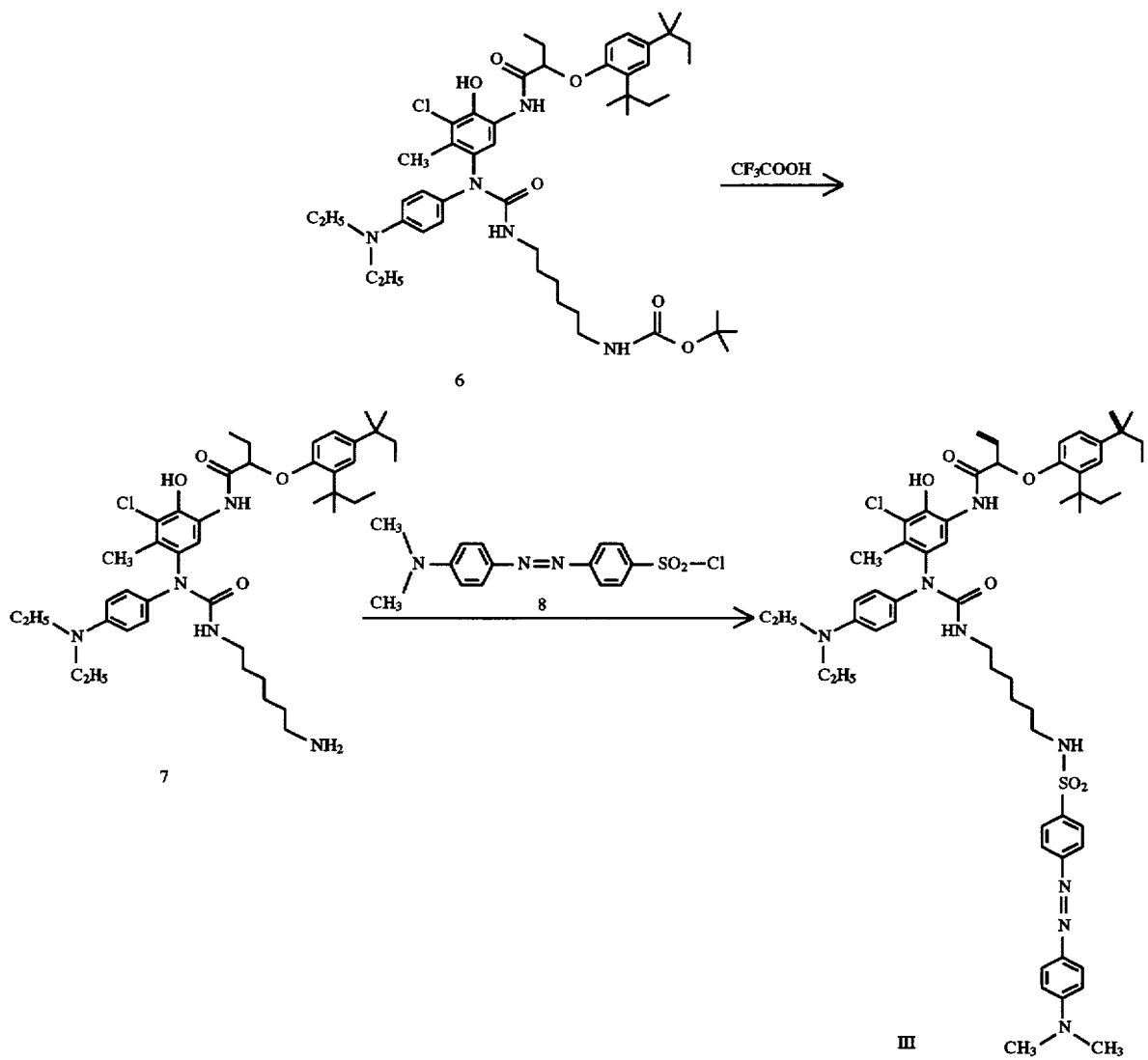

Synthesis of Blocked Developer C (4)

Carbamate (1) (33.97 g, 119.46 mmol) was dissolved in 250 mL toluene, and chlorotrimethylsilane (12.98 g, 119.46 mmol) and triethylamine (24.78 g, 244.89 mmol) were added. The mixture was refluxed for three hours, cooled to room temperature, and filtered to remove triethylammonium hydrochloride. The filtrate was added to a suspension of mono-protected diamine (3) (30.198 g, 119.46 mmol) and triethylamine (12.089 g, 119.46 mmol) in 500 mL toluene. The mixture was stirred at room temperature for two days. The solution was then filtered to remove the white solid. The white solid was dissolved in dichloromethane and extracted with water. The dichloromethane was washed with brine, dried over magnesium sulfate, and filtered. The solvent was removed in vacuo. The resulting solid was recrystallized from ethyl acetate/petroleum ether to give 33 g of blocked Developer C (4) in 68% yield.

Synthesis of Leuco Dye Intermediate (7)

Coupler K (5) (34.61 g, 70.42 mmol) and blocked Developer C (4) (26.66 g, 70.42 mmol) were dissolved in 840 mL dichloromethane. Sodium carbonate (141.81 g, 1337.97 mmol) was dissolved in 1000 mL water and added to the coupler/developer mixture in one portion. Potassium ferrocyanide (53.25 g, 126.05 mmol) and potassium ferricyanide (4.63 g, 14.08 mmol) were dissolved in 1000 mL water and added slowly dropwise over a 10 minute period. The reaction was allowed to stir for 30 minutes following addition. To the reaction was added three portions of potassium ferricyanide (4.64 g, 14.08 mmol) at 10 minute intervals. When addition was complete the mixture was stirred an additional 20 minutes and phase split. The organic layer was washed with water once and with brine once. The organic phase was separated, dried over magnesium sulfate, and filtered. The solvent was removed in vacuo. The product was purified by chromatography on a Waters Prep. 500 Liquid Chromatograph with 20% ethyl acetate/petroleum ether and the polarity was increased to 30% to elute leuco dye intermediate (6). Leuco dye intermediate (6) was stirred for 20 minutes with 60 mL trifluoroacetic acid. The solvent was removed in vacuo. The residue was dissolved in water and ethyl acetate and extracted twice with sodium bicarbonate solution and washed with water. After stirring and scratching, the product precipitated from the organic phase and was collected. The product was heated in ethyl acetate, cooled, and filtered to remove traces of purple color. After drying, 6.0 g of leuco dye intermediate (7) was obtained in 11.15% yield.

Conversion of Intermediate (7) to Redox-Yellow Dye-Releasing Compound III

A solution of leuco dye intermediate (7) (3.8 g, 5.0 mmol), dabsyl chloride (4-(dimethylamino)azobenzene-4'-sulfonyl chloride, from Tokyo Kasei Kogyo Co., Ltd., Tokyo, Japan, 2.2 g, 6.8 mmol), 1,8-diazabicyclo[5.4.0]undec-7-ene (3.0 g, 20 mmol) in DMF (30 mL), and pyridine (5 mL) was heated at 75° C. for 2 hours. The reaction mixture was then poured into 250 mL of saturated sodium chloride solution and the precipitate collected by filtration. After drying in vacuo, the precipitate was purified by chromatography to give 2.5 g of yellow dye-releasing compound III along with Compound VI.

Example 2

Preparation of Redox-Yellow Dye-Releasing Compound IV

The synthetic route to redox-dye-releasing compound IV is shown in Scheme II. The blocked synthesis involved reaction of coupler L with blocked developer B, which was prepared by reacting a hydroxy functionalized dye with 6-isocyanatohexyl protected 2-methyl-4-diethylaminoaniline.

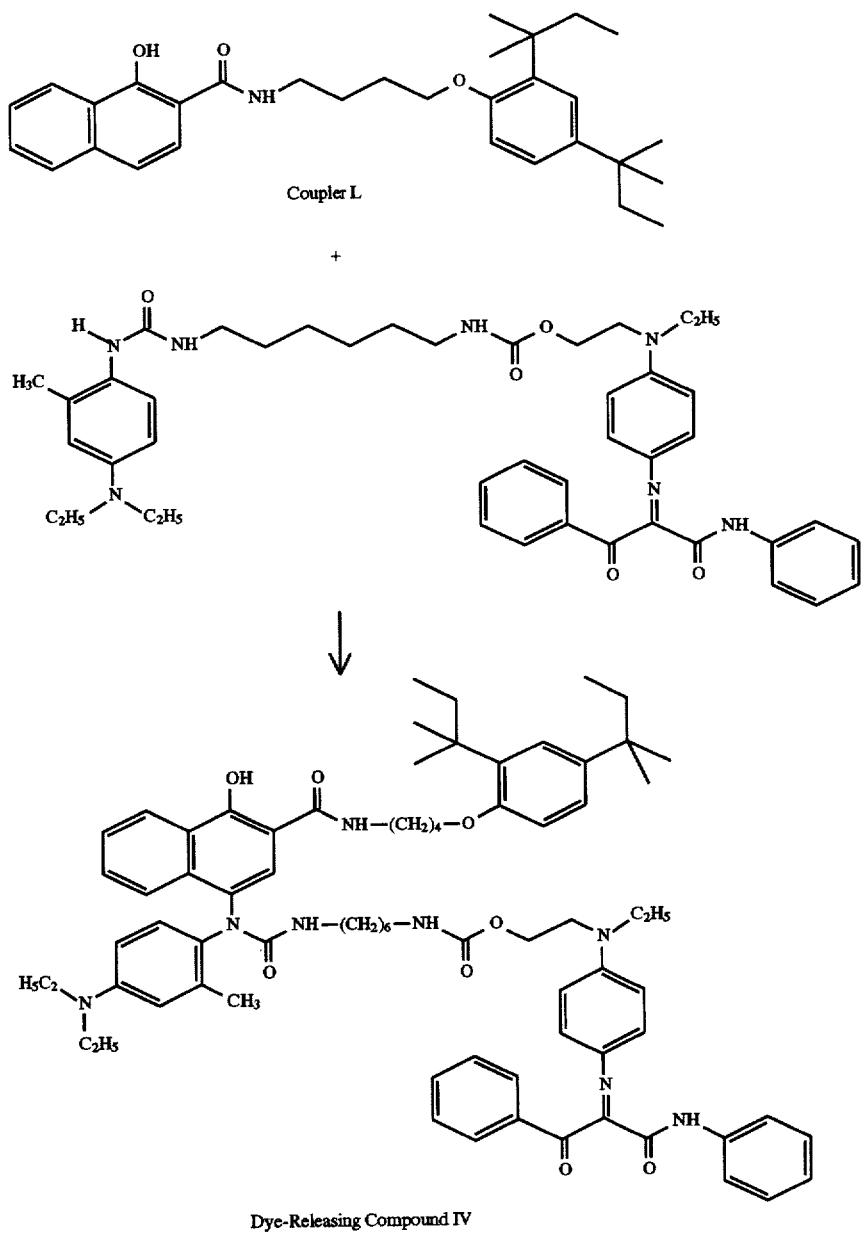

Synthesis of 6-Isocyanatohexyl Protected 2-Methyl-4-Diethylaminoaniline

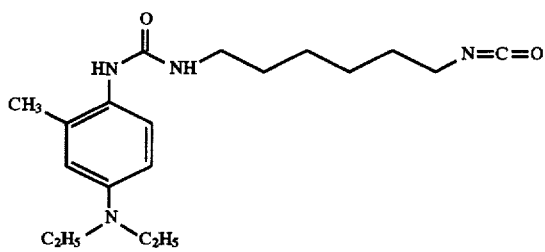

A solution of 2-methyl-4-diethylaminoaniline hydrochloride (95.5 g, 460 mmol) in 200 mL of $CH_2Cl_2$ and $Na_2CO_3$ (21.6 g, 460 mmol) in 100 mL of water was stirred for 0.5 hr in the presence of a small amount of $Na_2S_2O_4$ to prevent air oxidation. The layers were separated and the $CH_2Cl_2$ layer was dried over $K_2CO_3$, filtered and concentrated to afford free 2-methyl-4-diethylaminoaniline. 1,6-Diisocyanatohexane (75 g, 445 mmol) was taken up in 400 mL of THF. The free phenylenediamine was dissolved in 100 mL of THF and added to the diisocyanatohexane solution via a dropping funnel. The mixture was stirred and then maintained at room temperature overnight. The mixture was filtered, and the filtrate was concentrated, and the remaining solid was washed with petroleum ether and filtered again to provide very pure product. The original precipitate collected was composed of the desired product and bis-protected product. This was taken up in 1 L of THF, refluxed for 15 minutes, then filtered. The filtrate was concentrated to provide a solid, washed with ether, and filtered to provide the desired product. The solid filtered-off after refluxing also contained some of the desired product, however, further isolation was not pursued. Overall yield was 63 g (40%).

Synthesis of Dye 2

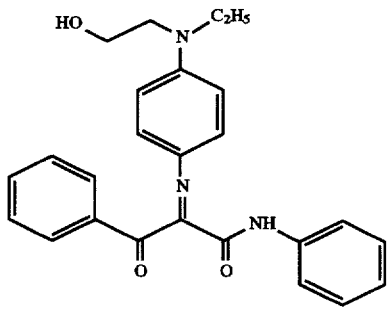

The hydroxy functionalized dye was prepared according to the method of Brown, G. H. *J. Amer. Chem. Soc.* 2919, (1957). Benzoylacetanilide (2.39 g, 10 mmol) was dissolved in 200 mL of ethanol. A solution of 5 g of sodium carbonate in 50 mL of water was added followed by 3.06 g of the N-ethyl-N-2-hydroxyethyl-1,4-phenylenediamine hydrogen sulfate developer in 50 mL of water. To the mixture was added a solution of 13.17 g (40 mmol) of $K_3Fe(CN)_6$ in 100 mL of water. The mixture stirred for 15 minutes and the dye was extracted with ethyl acetate, washed several times with water and concentrated in vacuo. A dark green solid resulted which was recrystallized from ethanol to provide 1.92 g (46% yield) of the desired product.

Synthesis of Dye-Protected Developer B

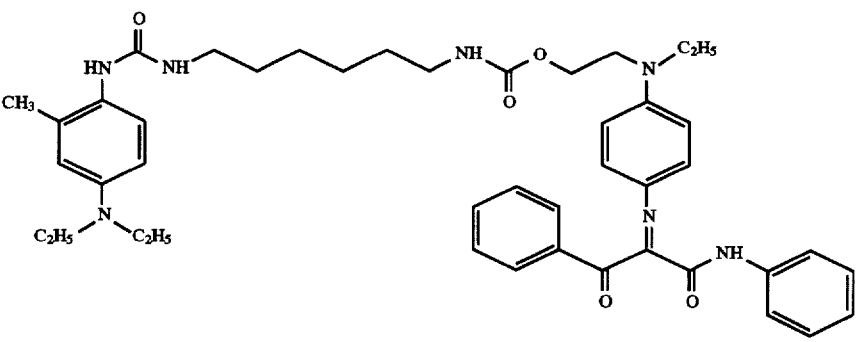

5.3 g (12.8 mmol) of Dye 2 and 4.6 g (14 mmol) of 6-isocyanatohexyl protected 2-methyl-4-diethylaminoaniline were combined with 1.9 g of dibutyltin dilaurate and 120 mL of toluene and refluxed for 2 hours. The mixture was cooled and the stirring was discontinued. After cooling, a yellow precipitate formed. This was washed first with hexane then with water. The resulting solid was dried under high vacuum to provide 7.6 g (78% yield) of the desired material.

Synthesis of Redox-Yellow Dye-Releasing Compound IV

Coupler L (2.33 g, 3.0 mmol) and blocked developer B (1.52 g, 3.2 mmol) containing the chromophore of a thermally mobile dye, i.e., dye-protected developer B, were dissolved in 70 mL of ethyl acetate. Addition of 140 mL of aqueous 5% sodium carbonate solution was followed by addition of 2.96 g of potassium ferricyanide $[K_3Fe(CN)_6]$. The mixture turned dark green after approximately 15 minutes. The solution was poured into a separatory funnel and the organic layer washed several times with water. The organic layer was separated, dried over anhydrous magnesium sulfate, filtered to remove drying agent, and concentrated. The resultant greenish oil was flash chromatographed twice on silica gel eluting with 1:1 hexanes/ethyl acetate to provide 0.75 g (20% yield) of Compound IV.

Example 3

Preparation of "Dry Silver" Photothermographic Constructions

Two different constructions were prepared using yellow dye-releasing compounds III and IV. Construction A consisted of a filled polyester (sold under the tradename Melinex™ 994 by ICI, Wilmington, Del.) base on which was coated a receptor layer, a blank emulsion, an interlayer, a photothermographic silver layer, and a topcoat layer. The wet coating thickness for each layer was 3 mils, except the photothermographic silver layer was 2 mils thick. Each layer was dried for 5 minutes at 180° F. (82° C.). Construction A and compound III were used in sample 1 (herein referred to as construction 1-A).

Construction B consisted of the same filled polyester base used in Construction A on which was coated a receptor layer, a photothermographic silver layer, and a topcoat layer. The wet coating thickness for each layer was 3 mils, except the photothermographic silver layer was either 2 mils or 3 mils thick. Each layer was dried for 5 minutes at 180° F. (82° C.). Construction B and compound III were used in samples 2–6 (herein referred to as constructions 2-B through 6-B). Construction B and compound IV were used in samples 7–8 (herein referred to as constructions 7-B and 8-B).

Receptor Layer: The receptor layer contained 15% by weight VYNS™-3 (copolymer of vinylchloride and vinylacetate available from Union Carbide, Danbury, Conn.) in methyl ethyl ketone and toluene (50:50).

Blank Emulsion Latter: The blank emulsion layer contained 100 g of a dispersion of silver behenate half soap (prepared as described in U.S. Pat. No. 5,262,272) at 10% solids homogenized in toluene and ethanol mixed with 360 g ethanol, 40 g acetone, 9 mL HgBr$_2$ solution (0.36 g/20 mL MeOH), 29 g Butvar™ B-76 (polyvinyl butyral available from Monsanto, St. Louis, Mo.), and 1.5 g FC-431 (aliphatic fluorocarbon surfactant available from Minnesota Mining and Manufacturing Company, St. Paul, Minn.).

Interlayer: The interlayer contained 2.0% polyvinyl alcohol polymer (Airvol™ 540 available from Air Products Corp.) in water and ethanol (50/50) and 2 drops of Fluorad™ FC-431 per 25 g of interlayer solution.

Photographic Silver Layer: A dispersion of a silver behenate full soap containing pre-formed silver halide grains (0.05 μm grain size, 9.0 mole % silver halide, and 98%:2% Br:I ratio of halides) was homogenized to 11.94% solids in a mixture of ethanol and toluene (76:24) and 0.48% polyvinyl butyral (Butvar™ B-76). To 200.0 g of the silver full soap dispersion was added 40.0 g of ethanol. After 10 minutes of mixing, an additional 32 g of the polyvinyl butyral was added. Three aliquots (0.055 g each) of pyridinium hydrobromide perbromide were added after 30, 60, and 90 minutes of mixing. After a final 4 hours of mixing, 1.3 mL of a 10% calcium bromide solution in methanol was mixed for 60 minutes. To 45 g of this silver solution was added 6.0 mL of the red sensitizing dye shown below (0.0100 g/36.6 mL toluene and 13.4 mL methanol, prepared according to U.S. Pat. No. 3,719,495). This solution is referred to herein as the red-sensitized silver premix.

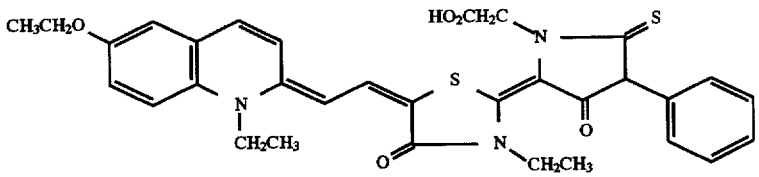

After 30 minutes, a solution of 2-(4-chlorobenzoyl) benzoic acid (0.0264 g for constructions 2-B to 6-B, or 0.0250 g for constructions 1-A, 7-B, and 8-B, and a mixture of N,N-bis[2-(4,6-tribromomethyl-1,3,5-triazino)-1,3-dipiperidinopropane "Antifoggant-1" and tris-tribromomethyl-s-triazine "Antifoggant-2" (0.033 g of a 95:5 mixture for constructions 1-A, or 0.0165 g of 65:35 mixture for constructions 2-B through 6-B), and tetrahydrofuran (1.2 mL) was added to the red-sensitized silver premix. For constructions 7-B and 8-B, 0.0124 g and 0.0062 g of the 95:5 mixture, respectively, were added to 6.69 g aliquots of the red-sensitized silver premix. The structures of Antifoggant-1 and Antifoggant-2, prepared according to Applicants' Assignee's copending allowed U.S. patent application Ser. No. 08/051,085 (filed Apr. 21, 1993), which is incorporated herein by reference, are shown below.

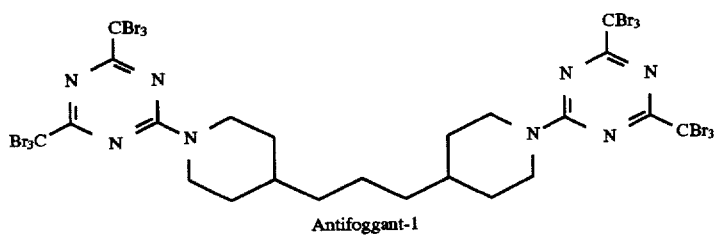

Antifoggant-1

-continued

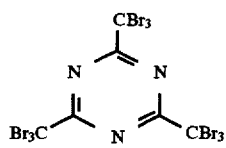

Antifoggant-2

After 15 minutes, a solution containing a yellow dye-releasing compound ($1.5 \times 10^{-4}$ moles of compound III or $1.875 \times 10^{-4}$ moles of compound IV), tetrahydrofuran (3.0 mL), aliphatic fluorocarbon surfactant FC-431 (0.1 mL), phthalazinone (0.075 g for constructions 1-A and 2-B), and the ammonium base precursor shown below ($7.5 \times 10^{-5}$ moles for construction 1-A only), was added to the red-sensitized silver premix. These resultant solutions are referred to herein as the silver halide solutions.

Base Precursor: A heterogeneous mixture of phthalic anhydride (10.0 grams, 67.51 mmoL) and 100 mL dichloromethane was cooled in an ice bath. n-Butylamine (12.345 grams, 168.78 mmoL) was added dropwise. The temperature was not allowed to go above 15° C. during the addition. When a small amount of the amine had been added a homogeneous solution was obtained. After a short time, a white precipitate was formed. As more amine was added the solution once again became homogeneous. When addition was complete the mixture was allowed to stir in an ice bath. After approximately ten minutes a white precipitate was formed. The mixture was stirred for 50 minutes at 0° C. and 10 minutes at room temperature. The solid was collected by filtration and washed with a small amount of dichloromethane. The solid was washed with hexane and air dried to give 8.86 grams of the desired material (shown below), characterized by $^1$H NMR.

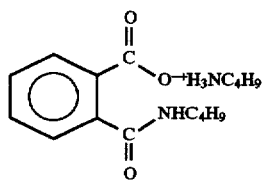

Topcoat: A topcoat solution was prepared containing 5.9% cellulose acetate (obtained from Eastman Kodak under the product number 398-6), 1.33% Rohm and Haas Acryloid™ A-21 in an acetone, isopropyl alcohol, and methanol mixture (11.67:2.72:1). For certain examples, the following toners were added to 123.75 g of the topcoat solution: phthalazine (0.436 g, PHZ), 4-methylphthalic acid (0.235 g, 4-MPA), and tetrabromophthalic anhydride (0.372 g, TBPAN). If these toners were used then phthalazinone was eliminated from the silver halide solution. The topcoat solution was coated at a wet thickness of 3 mil over the silver halide layer.

Example 4

Sensitometric Responses

All samples were exposed using an EG&G Sensitometer for $10^{-3}$ sec with a xenon flash through a #25 Wratten filter and a 0–3 continuous wedge. Generally, the coatings were processed with heat at dwell times of 10–60 seconds and a dwell temperature of 280° F. (138° C.) using a variable time and temperature roll processor.

Construction 1-A

Samples of construction 1-A were processed at either 280° F. (138° C.) or 290° F. (143° C.) for 30–40 seconds. The coated unexposed material appeared yellow because of the pre-formed yellow dye of dye-releasing compound III. Upon exposure and processing, a green dye image was observed in the photoimaged areas of the construction package, indicating that the —C(O)—NH— protecting group containing the dye cleaved to allow oxidation of the chromogenic leuco dye to the cyan dye. The sensitometric response as measured for this cyan image in the total donor and receptor construction is shown below:

| | Donor and Receptor Layers | | | | |
|---|---|---|---|---|---|
| | Dmin | Dmax | Speed-1 | Speed-2 | AC-1 |
| 30 sec/280° F. | 0.37 | 1.65 | 1.56 | 2.04 | 1.07 |
| 40 sec/280° F. | 0.59 | 1.45 | 1.21 | 1.75 | — |
| 40 sec/290° F. | 0.80 | 1.35 | 1.34 | — | — |

Upon removal of all the donor layers (only the receptor layer remained on the polyester base), a yellow dye image was observed in the receptor layer. This image corresponded to the photothermographic cyan image of the donor construction layers.

The sensitometric response was measured for the yellow dye within the receptor layer. As shown below, the photothermographic release of yellow dye from chromogenic leuco chemistry and diffusion of the thermally mobile dye through a multilayer construction into a receptor forms a yellow image. The final yellow dye image has been separated from the reactive silver and donor layers which may be discarded. The use of base is not necessary but does enhance the reactivity.

| | Receptor Layer Only | |
|---|---|---|
| | Dmin | Dmax |
| 30 sec/280° F. | 0.09 | 0.18 |
| 40 sec/280° F. | 0.11 | 0.28 |
| 40 sec/290° F. | 0.11 | 0.33 |

Construction 2-B

Samples of construction 2-B were processed at 280° F. (138° C.) for 10–40 seconds. The unprocessed material was yellow in color because of the presence of the chromophore of the thermally mobile yellow dye of redox-dye-releasing compound III. After processing, a green image was observed in the photo-imaged areas only. The sensitometry of these material in the donor and receptor layers are shown below:

| | Donor + Receptor | | | | |
|---|---|---|---|---|---|
| | Dmin | Dmax | Speed-1 | Speed-2 | AC-1 |
| 10 sec/280° F. | 0.19 | 0.52 | 3.31 | — | — |
| 20 sec/280° F. | 0.21 | 1.01 | 2.88 | 3.36 | — |
| 30 sec/280° F. | 0.23 | 1.41 | 2.59 | 3.08 | 1.09 |
| 40 sec/280° F. | 0.31 | 1.67 | 2.10 | 2.82 | 0.91 |

Formation of cyan dye suggested that the chromogenic leuco dye had been oxidized and the blocking group containing the chromophore of the yellow thermally mobile dye cleaved. In this construction, however, both the cyan dye from the oxidized chromogenic portion and the released yellow dye diffused to the receptor. Also, because compound III diffused both during the coating process and during processing, a yellow dye color was present throughout the receptor layer in both imaged and non-imaged areas. After removal of the donor layers the following sensitometry was measured for both cyan and yellow dyes in the receptor:

| | | Receptor | | |
|---|---|---|---|---|
| | | Dmin | Dmax | Speed-1 |
| 10 sec/280° F. | Red | 0.10 | 0.15 | — |
| | Blue | 1.74 | 1.78 | — |
| 20 sec/280° F. | Red | 0.11 | 0.30 | — |
| | Blue | 1.71 | 1.84 | — |
| 30 sec/280° F. | Red | 0.12 | 0.38 | 3.21 |
| | Blue | 1.65 | 1.92 | — |
| 40 sec/280° F. | Red | 0.14 | 0.56 | 2.95 |
| | Blue | 1.69 | 1.95 | — |

In an attempt to determine reaction products, construction 2-B was exposed for 60 seconds using a tungsten light source on a Omega Super Chromonega D Dichroic II enlarger using no correction filters. The material was then processed for 60 seconds at 280° F. (138° C.). This blanket exposure and processing resulted in green color formation suggesting that cleavage of the —C(O)—NH— protecting group containing the thermally mobile dye had occurred.

The cleavage products and other materials were identified and molar fraction of each species determined by the following method. The donor was separated from the receptor layer. Each layer was dissolved in ethyl acetate and filtered. Petroleum ether was added to the filtrate, so that the solvent was composed of 3:2 ratio of petroleum ether to ethyl acetate. The mixture was again filtered and concentrated in vacuo. The product was chromotographed on silica gel with ethyl acetate and petroleum ether. Thin layer chromatography further purified the isolated materials.

Three materials were isolated from photothermographic constructions containing redox-dye-releasing compound III. The first of these, compound V, results from oxidation of redox-dye-releasing compound III and was formed from cleavage of the protecting group. The second material, compound VI, was originally present in compound III as an impurity. Compound VI resulted from reaction of the dabsyl chloride with DBU, which is used as a catalyst in the preparation of redox-dye-releasing compound III. Unreacted compound III was also isolated. The structures of compounds V and VI are as follows:

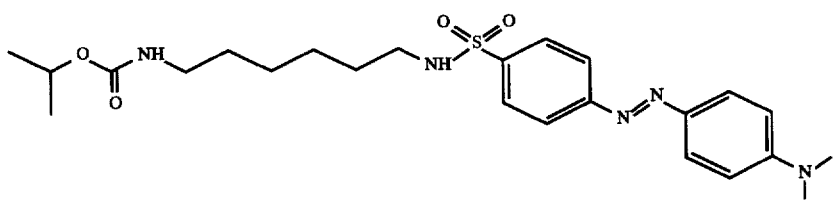

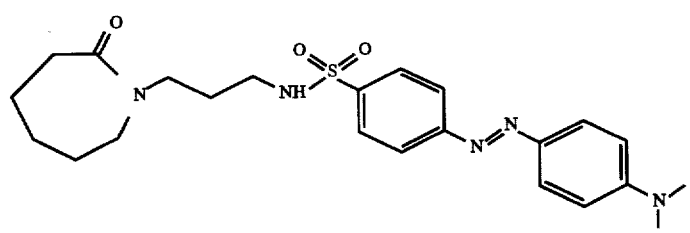

The structure of cleavage product V was confirmed through $^1$H NMR spectroscopy, mass spectroscopy, and comparison to an authentic sample. The isopropyl group came from residual isopropyl alcohol used as the solvent in the topcoat. Other alcohols could also be added to produce a different diffusible product.

Integration of NMR spectra of material isolated from the donor and receptor layers, respectively, provided data on the relative amounts of each species present in the processed film. UV-vis spectroscopy quantified total dye present in the donor and in the receptor. In a sample of unprocessed film, 69% of the total yellow density was in the donor and 31% was in the receptor. After exposure and processing, 50% of the yellow density was in the receptor and 50% was in the donor layer. This measurement related material present in the donor layer to material present in the receptor, as shown below. Molar fraction of each species present in the donor and receptor layers of the photothermographic construction total of all species containing the dabsyl chloride chromophore was 1.00.

| | III | V | VI |
|---|---|---|---|
| Donor | 0.14 | 0.36 | 0 |
| Receptor | 0.11 | 0.29 | 0.10 |

Approximately 4% of the initial density could not be extracted from the donor and receptor.

Constructions 3-B through 6-B

Using construction B, the redox-dye-releasing compound III was studied using the 65:35 mixture of Antifoggant-1 and Antifoggant-2. Construction 3-B contained PAZ toner, construction 4-B contained PAZ toner and ½ molar equivalent base precursor (see Example 1), construction 5-B contained PHZ/4MPA/TBPAN toners, and construction 6-B contained PHZ/4MPA/TBPAN toners and ½ molar equivalent base precursor. These coatings were exposed and processed as described above. A green photothermographic image was observed in all the coatings which suggested cleavage of the —C(O)—NH— protecting group containing the chromophore of the yellow thermally mobile dye.

The sensitometric responses for the total construction and the cyan dye color formation are shown below. The results suggest the addition of base enhances the cleavage of the —C(O)—NH— protecting group moiety and thus facilitates release of the yellow dye.

| Donor and Receptor | | | | | |
|---|---|---|---|---|---|
| 20 sec/280° F. | Dmin | Dmax | Speed-1 | Speed-2 | AC-1 |
| PAZ toner | | | | | |
| 3-B | 0.22 | 0.97 | 2.97 | 3.41 | — |
| 4-B | 0.20 | 1.84 | 1.46 | 1.85 | 1.21 |
| PHZ/4-MPA/-TBPAN | | | | | |
| 5-B | 0.21 | 1.09 | 2.54 | 3.12 | 0.35 |
| 6-B | 0.37 | 1.72 | 1.81 | 2.28 | 0.84 |

Constructions 7-B and 8-B

Using construction B, the redox-dye-releasing compound IV was studied using the 95:5 mixture of Antifoggant-1 and Antifoggant-2 material and the PHZ/4-MPA/TBrPAN toners. The coatings were exposed and processed for 20 to 40 seconds at 280° F. (138° C.). The unprocessed material was yellow in color because of the presence of the chromophore of the yellow thermally mobile dye of compound IV. After processing, a green dye image was observed in the photo imaged areas only.

The sensitometry of these materials in the donor and receptor layers is shown below. Formation of cyan dye suggests that the chromogenic leuco dye has been oxidized and the blocking group containing the chromophore of the yellow thermally mobile dye cleaved. In this construction, though, both the cyan dye and the released dye diffused to the receptor. Also, the starting material compound IV diffused during the coating process and during processing. Therefore, a yellow dye color was present throughout the receptor layer in both the imaged and non-imaged areas.

| Donor + Receptor | | | | |
|---|---|---|---|---|
| | Processing Conditions | Dmin | Dmax | Speed-1 |
| Construction 7-B | 20 sec/280° F. | 0.18 | 0.65 | 2.51 |
| | 30 sec/280° F. | 0.18 | 0.89 | 2.18 |
| | 40 sec/280° F. | 6.21 | 1.03 | 1.97 |
| Construction 8-B | 20 sec/280° F. | 0.19 | 0.83 | 2.26 |
| | 30 sec/280° F. | 0.35 | 1.08 | 2.08 |

After removal of the donor layers, the following sensitometry was measured for both cyan and yellow dyes in the receptor. In the area corresponding to the photoimaged exposure, a green image was observed. With increasing processing time, more of the dyes are diffused to the receptor.

| Donor and Receptor | | | | |
|---|---|---|---|---|
| | Processing Conditions | Dmin | Dmax | Speed-1 |
| Construction 7-B | 20 sec/280° F. Red | 0.12 | 0.24 | — |
| | Blue | 1.02 | 1.04 | — |
| | 30 sec/280° F. Red | 0.13 | 0.33 | — |
| | Blue | 1.03 | 1.08 | — |
| | 40 sec/280° F. Red | 0.13 | 0.38 | 3.01 |
| | Blue | 1.05 | 1.12 | — |
| Construction 8-B | 20 sec/280° F. Red | 0.13 | 0.27 | — |
| | Blue | 1.04 | 1.11 | — |
| | 30 sec/280° F. Red | 0.15 | 0.37 | 3.26 |
| | Blue | 1.03 | 1.12 | — |

The disclosures of all publications, patents, and patent applications listed herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A chromogenic leuco redox-dye-releasing compound of the formula:

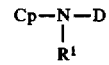

wherein:

(a) Cp is a coupler group;

(b) N—D is a photographic developer obtained from a primary amine color photographic developer group; and (c) $R^1$ is a —C(O)—NH—A—Dye group, wherein: Dye represents the chromophore of a thermally mobile dye; and A represents a single bond or a divalent linking group of the formula —X—$R^5$—L—, wherein $R^5$ is a divalent hydrocarbon chain containing up to 12 carbon atoms, L is a single bond or a divalent group that binds the chromophore of the thermally mobile dye to $R^5$, and X represents a single bond or an —$SO_2$— group.

2. The dye-releasing compound of claim 1 wherein $R^5$ is a divalent aliphatic group containing 1–12 carbon atoms or a divalent aromatic group containing 5–12 carbon atoms.

3. The dye-releasing compound of claim 2 wherein $R^5$ is an alkylene group containing 1–8 carbon atoms.

4. The dye-releasing compound of claim 1 wherein Cp is a photographic coupler group.

5. A chromogenic leuco redox-dye-releasing compound of the general formula:

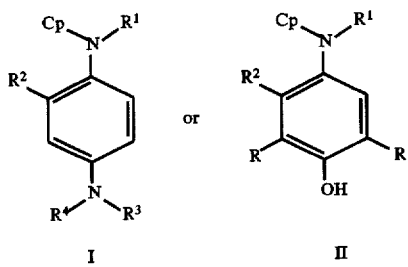

wherein:

(a) R is hydrogen or halogen;

(b) $R^1$ is a —C(O)—NH—A—Dye group, wherein: Dye represents the chromophore of a thermally mobile dye; and A represents a single bond or a divalent linking group of the formula —X—$R^5$—L—, wherein $R^5$ is a divalent hydrocarbon chain containing up to 12 carbon atoms, L is a single bond or a divalent group that binds the chromophore of the thermally mobile dye to $R^5$, and X represents a single bond or an —$SO_2$— group;

(c) $R^2$ is a hydrogen atom, an alkoxy group, an alkyl group, or a ballasting group;

(d) $R^3$ and $R^4$ are each independently an aliphatic group, an aromatic group, or a —Z—Y group, wherein Z is an alkylene group containing 1–4 carbon atoms, and Y is a cyano group, a halogen atom, an alkoxy group containing 1–20 carbon atoms, or —OH; and (e) Cp is a coupler group.

6. The dye-releasing compound of claim 5 wherein Cp is a photographic coupler group.

7. The dye-releasing compound of claim 5 wherein $R^2$ is a hydrogen atom, an alkoxy group containing 1–20 carbon atoms, or an alkyl group containing 1–20 carbon atoms.

8. The compound of claim 1 wherein N—D is a photographic developer group obtained from a primary aromatic amine color photographic developer.

9. The compound of claim 4 wherein the coupler group contains a ballasting group.

10. The compound of claim 1 wherein the developer group contains a ballasting group.

11. The compound of claim 1 wherein Dye is the chromophore of an azo dye, azomethine dye, azamethine dye, anthraquinone dye, naphthoquinone dye, styryl dye, nitro dye, benzylidene dye, oxazine dye, diazine dye, thiazine dye, ketazine dye, imidazole dye, indoaniline dye, merocyanine dye, benzodifuranone dye, quinoline dye, indophenol dye, or a triphenylmethane dye.

* * * * *